(12) United States Patent
Kimura et al.

(10) Patent No.: US 11,911,466 B2
(45) Date of Patent: *Feb. 27, 2024

(54) SUBSTITUTED PYRIMIDINES AS VACCINE ADJUVANTS

(71) Applicant: Sumitomo Pharma Co., Ltd., Osaka (JP)

(72) Inventors: Hidenori Kimura, Tokyo (JP); Hitoshi Ban, Osaka (JP); Yoshiaki Isobe, Osaka (JP); Hitoshi Watanabe, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 19 days.

This patent is subject to a terminal disclaimer.

(21) Appl. No.: 17/583,933

(22) Filed: Jan. 25, 2022

(65) Prior Publication Data

US 2022/0226468 A1 Jul. 21, 2022

Related U.S. Application Data

(60) Division of application No. 16/822,894, filed on Mar. 18, 2020, now Pat. No. 11,266,738, which is a continuation of application No. 15/766,560, filed as application No. PCT/JP2016/079756 on Oct. 6, 2016, now Pat. No. 10,632,192.

(30) Foreign Application Priority Data

Oct. 7, 2015 (JP) ................................ 2015-199750

(51) Int. Cl.
 C07D 239/49 (2006.01)
 A61K 39/39 (2006.01)
 A61K 39/00 (2006.01)
 A61P 37/04 (2006.01)

(52) U.S. Cl.
 CPC .............. *A61K 39/39* (2013.01); *A61K 39/00* (2013.01); *A61P 37/04* (2018.01); *C07D 239/49* (2013.01); *A61K 2039/505* (2013.01)

(58) Field of Classification Search
 CPC .................................................. C07D 239/49
 USPC ....................................................... 544/325
 See application file for complete search history.

(56) References Cited

U.S. PATENT DOCUMENTS

| 4,689,338 | A | 8/1987 | Gerster |
| 10,632,192 | B2 | 4/2020 | Kimura et al. |
| 2018/0280499 | A1 | 10/2018 | Kimura |

FOREIGN PATENT DOCUMENTS

| EP | 3360864 | 8/2018 |
| JP | 2011-506276 | 3/2011 |
| JP | 2012-507502 | 3/2012 |
| JP | 2013-534248 | 9/2013 |
| JP | 2015-520729 | 7/2015 |
| RU | 2014113236 | 10/2015 |
| WO | WO 200012487 | 9/2000 |
| WO | WO 2005001022 | 1/2005 |
| WO | WO 2005018555 | 3/2005 |
| WO | WO 2009067081 | 5/2009 |
| WO | WO 2010048520 | 4/2010 |
| WO | WO 2010093436 | 8/2010 |
| WO | WO 2010133885 | 11/2010 |
| WO | WO 2011017611 | 2/2011 |
| WO | WO 2011139348 | 11/2011 |
| WO | WO 2012024284 | 2/2012 |
| WO | WO 2012066335 | 5/2012 |
| WO | WO 2012066336 | 5/2012 |
| WO | WO 2012067268 | 5/2012 |
| WO | WO 2012067269 | 5/2012 |
| WO | WO 2013172479 | 11/2013 |

OTHER PUBLICATIONS

Arias et al., "Squalene Based Nanocomposites: A New Platform for the Design of Multifunctional Pharmaceutical Theragnostics", ACS NANO, vol. 5, No. 2, 1513-1521, 2011.

Dorwald, F. Zaragoza, Side Reactions in Organic Synthesis: A Guide to Successful Synthesis Design, Weinheinn: WILEY-VCH Verlag GmbH & Co. KGaA, 2005, Preface, 6 pages.

(Continued)

*Primary Examiner* — Douglas M Willis

(74) *Attorney, Agent, or Firm* — Fish & Richardson P.C.

(57) ABSTRACT

The present invention provides a compound of the formula (1):

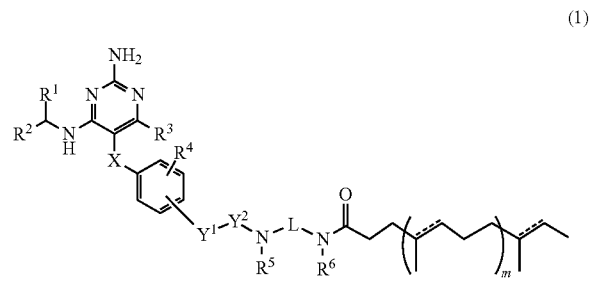

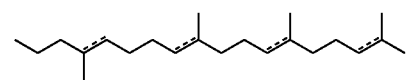

wherein X, $R^1$, $R^2$, $R^3$, $R^4$, $R^5$, $R^6$, $Y^1$, $Y^2$, L, and m are as defined in the description, and a pharmaceutically acceptable salt thereof, which are useful as a vaccine adjuvant.

27 Claims, 5 Drawing Sheets

(56) References Cited

OTHER PUBLICATIONS

EP Extended European Search Report in European Appln. No. 16853686.0, dated Apr. 30, 2019, 4 pages.
Extended European Search Report in European Appln. No. 21164640.1, dated Jul. 22, 2021, 10 pages.
Fox, "Squalene Emulsions for Parenteral Vaccine and Drug Delivery", Molecules, 14, 3286-3312, 2009.
Goff et al., "Synthetic Toll-Like Receptor 4 (TLR4) and TLR7 Ligands as Influenza Virus Vaccine Adjuvants Induce Rapid, Sustained, and Broadly Protective Responses", Journal of Virology, vol. 89, No. 6, 3221-3235, 2015.
International Search Report and Written Opinion in International Application No. PCT/JP2016/079756, dated Dec. 20, 2016, 8 pages.
Iwasaki et al., "Toll-like receptor control of the adaptive immune responses", Nature Immunology, vol. 5, No. 10, 987-995, 2004.
Jordan, V. C. Nature Reviews: Drug Discovery, 2, 2003, 205.
O'Hagan et al., "The mechanism of action of MF59 - An innately attractive adjuvant formulation", Vaccine, 30, 4341-4348, 2012.
Ott et al., "The Adjuvant MF59: A 10-Year Perspective", Methods in Molecular Medicine, vol. 42, 211-228, 2000.
RU Office Action and Search Report in Russian Appln. No. 2018116351, dated Feb. 25, 2020, 11 pages.
Smirnov et al., "Vaccine adjuvant activity of 3M-052: An imidazoquinoline designed for local activity without systemic cytokine induction", Vaccine, 29, 5434-5442, 2011.
Steinhagen et al., "TLR-based immune adjuvants", Vaccine, 29, 3341-3355, 2011.
Tomai et al., "Resiquimod and other immune response modifiers as vaccine adjuvants", Expert Rev. Vaccins, 6(5), 835-847, 2007.
Valetti et al., "Peptide Conjugation: Before or After Nanoparticle Formation?", Bioconjugate Chemistry, 25, 1971-1983, 2014.
Office Action in Canadian Appln. No. 3,001,283, dated Nov. 9, 2022, 7 pages.

SUBSTITUTED PYRIMIDINES AS VACCINE ADJUVANTS

TECHNICAL FIELD

The present invention relates to a compound useful as a vaccine adjuvant, a method for producing the same, a composition comprising the same, and a use of the same as a vaccine adjuvant.

BACKGROUND

Vaccines comprising a protein or a partial peptide, which are originated from proteins or partial peptides produced by microorganisms, can be produced using chemical synthesis or genetic recombination technology and are advantageous in terms of safety and process for the production. On the other hand, however, subunit vaccines comprising a partial peptide (epitope) tend to have lower immuno-stimulating ability than that of live vaccines and inactivated vaccines. Therefore, in order to enhance the immunogenicity of the epitope and to improve the immuno-stimulating activity of the vaccine, it has been investigated for prophylactic or therapeutic methods using an adjuvant and an antigen in combination.

Adjuvants are an additive to enhance humoral and/or cellular immune responses to antigens, and Alum, saponin, etc. have been used as an vaccine adjuvant.

Recently, it was revealed that Toll-like Receptor (TLR) plays an important role in the activation of innate immunity, which is a defense mechanism in living organisms against microorganisms, and that monophosphoryl lipid A (MPL), CPG ODN, etc., showed immuno-stimulating effect via TLR.

Of the known thirteen TLRs identified in human, five TLRs (TLRs 1, 2, 4, 5 and 6) are involved in recognition of bacterial components, and four TLRs (TLRs 3, 7, 8 and 9) are localized in cytoplasmic compartment and are involved in recognition of viral RNA (TLR 3, 7, 8) and unmethylated DNA (TLR 9) (see Non Patent Document 1).

As an agonist (activator) of TLR7 and TLR8, small molecules that mimic a single-stranded RNA of virus, which is a natural ligand, has been known. For example, synthetic compounds, such as pyrimidine compounds (Patent Documents 1 and 2) and imidazoquinoline compounds (Patent Document 3), have been reported.

Activation of TLR7 and/or TLR8 with its agonist induces Th1 cells and activates dendritic cells (DC) via TLR/MyD88-dependent signaling pathway. As a result, the expression of the T cell co-stimulatory molecules (CD80, CD86, CD40) is enhanced, and inflammatory cytokines including type I interferon (especially IFNα), TNFα, IL-6 or IL-12 are produced.

In addition to the activation of DC, the TLR7 and/or TLR8 agonist (activator) was known to activate B cells and further stimulate NK cells to promote IFNγ production, and therefore it is expected to have a vaccine adjuvant activity. Indeed, adjuvant activity of TLR7/TLR8 agonists, such as Resiquimod and Imiquimod, has been reported (Non Patent Document 2).

From the above, there is need for development of new vaccine adjuvant that activates TLR7 and/or TLR8.

On the other hand, squalene is an oily substance used as an oil component for oil-in-water and water-in-oil emulsion preparations, and a squalene-containing adjuvant such as MF59 has been used as an adjuvant for influenza vaccine (Non Patent Documents 3, 4 and 5).

As for conjugates of TLR7/8 agonists and another substances, vaccine adjuvants wherein an imidazoquinoline compound are covalently linked to a fatty acid (Patent Documents 4, 5, 6 and Non-Patent Document 6), conjugates of an imidazoquinoline compound and a fatty acid glyceride (Patent Document 7), conjugates of an adenine compound and a fatty acid glyceride (Patent Document 8), and conjugates of an adenine compound and a phospholipid (Patent Document 9) were known. Also, conjugates wherein an adenine compound is conjugated with a fatty acid glyceride via polyethylene glycol were known (Patent Document 10).

However, a conjugate of TLR7/8 agonist and squalene was not known.

PRIOR ART DOCUMENTS

Patent Documents

[Patent Document 1] WO00/12487
[Patent Document 2] WO2009/067081
[Patent Document 3] U.S. Pat. No. 4,689,338
[Patent Document 4] WO2005/001022
[Patent Document 5] WO2005/018555
[Patent Document 6] WO2012/024284
[Patent Document 7] WO2010/048520
[Patent Document 8] WO2011/017611
[Patent Document 9] WO2011/139348
[Patent Document 10] WO2010/093436

Non Patent Document

[Non Patent Document 1] Iwasaki, A., Nat. Immunol. 2004, 5, 987
[Non Patent Document 2] Vaccine 2011, 29, 3341•M. A. Tomai et al, Exp. Rev. Vaccine, 6, 835
[Non Patent Document 3] G. Ott et al. Methods in Molecular Medicine, 2000, 42, 211-228
[Non Patent Document 4] D. T. O'Hagan et al. Vaccine 2012, 4341-4348
[Non Patent Document 5] C. B. Fox, molecules 2009, 14, 3286
[Non Patent Document 6] Vaccine 2011, 29, 5434

SUMMARY OF INVENTION

Problem to be Solved by the Invention

The present invention provides a compound useful as a vaccine adjuvant, a method for producing the same, and a composition comprising the same.

Solution to Problem

As a result of dedicated studies, the present inventors discovered that a conjugated compound, in which a pyrimidine compound which enhances the physiological activity (function) of Toll-like Receptor 7 (TLR7) is chemically conjugated to an oily substance via a spacer, has an adjuvant activity superior than that of the pyrimidine compound or the oily substance alone and have accomplished the present invention based on this discovery.

The present invention is as set forth below.

[1] A compound of the formula (1) or a pharmaceutically acceptable salt thereof:

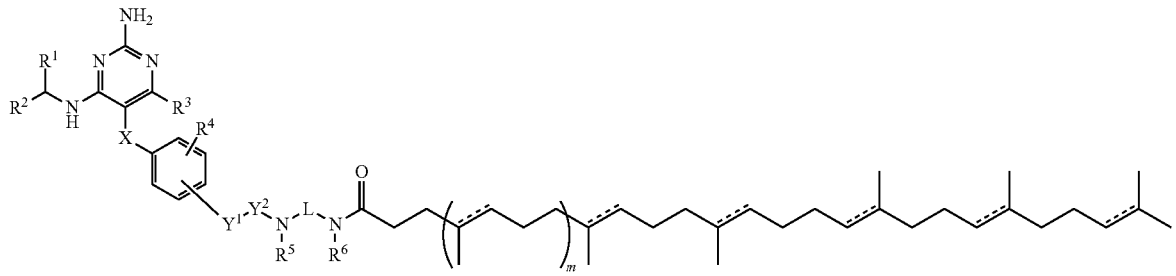

(1)

wherein
X is methylene, oxygen atom, sulfur atom, SO, SO$_2$ or NR$^7$ wherein R$^7$ is hydrogen atom or an alkyl group of 1 to 3 carbon atoms;

R$^1$ and R$^2$ are independently hydrogen atom or a substituted or unsubstituted alkyl group of 1 to 6 carbon atoms, provided that when the alkyl group is substituted, it is substituted with 1 to 4 same or different substituents selected from the group consisting of hydroxy group, halogen atom, and an alkoxy group of 1 to 6 carbon atoms;

R$^3$ is an alkyl group of 1 to 6 carbon atoms, an alkoxy group of 1 to 6 carbon atoms or an alkylthio group of 1 to 6 carbon atoms;

R$^4$ is hydrogen atom, halogen atom, hydroxy group, an alkyl group of 1 to 6 carbon atoms, an alkoxy group of 1 to 6 carbon atoms or cyano group;

Y$^1$ is a single bond, —(CR$^9$R$^{10}$)$_p$—, —CH=CH—(CR$^9$R$^{10}$)$_q$—, —C≡C—(CR$^9$R$^{10}$)$_{q'}$— or —(CR$^9$R$^{10}$)$_r$—O—(CR$^{9'}$R$^{10'}$)$_{r'}$— wherein R$^9$, R$^{10}$, R$^{9'}$, and R$^{10'}$ are independently hydrogen atom or an alkyl group of 1 to 4 carbon atoms;

Y$^2$ is a single bond or —C(O)—;

L is a substituted or unsubstituted straight chain alkylene of 2 to 6 carbon atoms or a divalent group derived from 4- to 8-membered cycloalkane, provided that when the straight chain alkylene or the cycloalkane is substituted, it is substituted with 1 to 4 same or different substituents selected from the group consisting of alkyl group of 1 to 5 carbon atoms, hydroxy group and halogen atom, and any one of the methylene group in the straight chain alkylene of L is optionally replaced with carbonyl group;

R$^5$ and R$^6$ are independently hydrogen atom or a substituted or unsubstituted alkyl group of 1 to 6 carbon atoms, or either R$^5$ or R$^6$ is bonded to any carbon atom of L to form a 4- to 8-membered nitrogen-containing saturated heterocycle, or R$^5$ and R$^6$ are taken together to form a substituted or unsubstituted 5- to 8-membered nitrogen-containing saturated heterocycle; provided that when the alkyl group is substituted, it is substituted with same or different 1 to 4 substituents selected from the group consisting of hydroxy group and halogen atom; when the 4- to 8-membered nitrogen-containing saturated heterocycle or the 5- to 8-membered nitrogen-containing saturated heterocycle is substituted, it is substituted with same or different 1 to 4 substituents selected from the group consisting of methyl group, ethyl group, propyl group, hydroxymethyl group, hydroxyethyl group, carbonyl group, hydroxy group and halogen atom;

m is 0 or 1;
p is an integer of 1 to 6;
q and q' are independently an integer of 0 to 4;
r is an integer of 0 to 5, and r' is an integer of 1 to 5, provided that r' is an integer of 2 or more when the sum of r and r' is 5 or less and Y$^2$ is a single bond; and

- - - - - - is independently a single bond or a double bond.

[2] The compound or a pharmaceutically acceptable salt thereof according to [1] wherein X is methylene, oxygen atom or NR$^7$ wherein R$^7$ is hydrogen atom or an alkyl group of 1 to 3 carbon atoms; R$^1$ and R$^2$ are independently hydrogen atom or a substituted or unsubstituted alkyl group of 1 to 6 carbon atoms, provided that when the alkyl group is substituted, it is substituted with 1 to 4 same or different substituents selected from the group consisting of hydroxy group and halogen atom; R$^3$ is an alkyl group of 1 to 6 carbon atoms; and R$^4$ is hydrogen atom, halogen atom, hydroxy group, an alkyl group of 1 to 3 carbon atoms or an alkoxy group of 1 to 3 carbon atoms.

[3] The compound or a pharmaceutically acceptable salt thereof according to [1] or [2] wherein - - - - - - are all single bonds or all double bonds.

[4] The compound or a pharmaceutically acceptable salt thereof according to any one of [1] to [3] wherein Y$^1$ is a single bond or —(CR$^9$R$^{10}$)$_p$— wherein R$^9$ and R$^{10}$ are independently hydrogen atom or an alkyl group of 1 to 4 carbon atoms; and Y$^2$ is a single bond or —C(O)—.

[5] The compound or a pharmaceutically acceptable salt thereof according to [4] wherein Y$^1$ is a single bond; and Y$^2$ is —C(O)—.

[6] The compound or a pharmaceutically acceptable salt thereof according to [4] wherein Y$^1$ is —(CR$^9$R$^{10}$)$_p$— wherein R$^9$ and R$^{10}$ are independently hydrogen atom or an alkyl group of 1 to 4 carbon atoms; p is an integer of 1 to 3; and Y$^2$ is a single bond.

[7] The compound or a pharmaceutically acceptable salt thereof according to [3] wherein Y$^1$ is —(CR$^9$R$^{10}$)$_r$—O—(CR$^{9'}$R$^{10'}$)$_{r'}$— wherein R$^9$, R$^{10}$, R$^{9'}$ and R$^{10'}$ are independently hydrogen atom or an alkyl group of 1 to 4 carbon atoms; and r and r' are independently 0, 1 or 2.

[8] The compound or a pharmaceutically acceptable salt thereof according to any one of [1] to [7] wherein L is a straight chain alkylene of 2 or 3 carbon atoms.

[9] The compound or a pharmaceutically acceptable salt thereof according to [1]
wherein
X is methylene;
R$^1$ is hydrogen atom or an alkyl group of 1 to 3 carbon atoms optionally substituted with hydroxyl group;

R² is hydrogen atom or an alkyl group of 1 to 6 carbon atoms;

R³ is an alkyl group of 1 to 3 carbon atoms;

R⁴ is hydrogen atom, halogen atom, hydroxy group, an alkyl group of 1 to 3 carbon atoms or an alkoxy group of 1 to 3 carbon atoms;

Y¹ is a single bond or methylene;

Y² is a single bond or —C(O)—;

L is a straight chain alkylene of 2 or 3 carbon atoms;

R⁵ and R⁶ are independently hydrogen atom or an alkyl group of 1 to 3 carbon atoms, or R⁵ and R⁶ are taken together to form a substituted or unsubstituted 5- to 8-membered nitrogen-containing saturated heterocycle, provided that when the 5- to 8-membered nitrogen-containing saturated heterocycle is substituted, it is substituted with same or different 1 to 4 substituents selected from the group consisting of hydroxy group and halogen atom;

m is 0 or 1; and

------ are all double bond.

[10] A pharmaceutical composition comprising the compound or a pharmaceutically acceptable salt thereof according to any one of [1] to [9].

[11] The pharmaceutical composition according to [10] comprising further an antigen.

[12] The pharmaceutical composition according to [11] wherein the antigen is a pathogen-derived antigen or a tumor antigen.

[13] The pharmaceutical composition according to [11] or [12] wherein the antigen is a peptide or a protein.

[14] A vaccine adjuvant comprising the compound or a pharmaceutically acceptable salt thereof according to any one of [1] to [9].

[15] The compound or a pharmaceutically acceptable salt thereof according to any one of [1] to [9] for use as a vaccine adjuvant.

[16] A method for enhancing an antigen-specific immune reaction in a mammal, comprising administering the compound or a pharmaceutically acceptable salt thereof according to any one of [1] to [9] to the mammal.

[17] A method for improving the immune response ability of a mammal, comprising administering the compound or a pharmaceutically acceptable salt thereof according to any one of [1] to [9] to the mammal.

[18] Use of the compound or a pharmaceutically acceptable salt thereof according to any one of [1] to [9] for the manufacture of a vaccine adjuvant.

[19] A compound of the formula (2) or a pharmaceutically acceptable salt thereof:

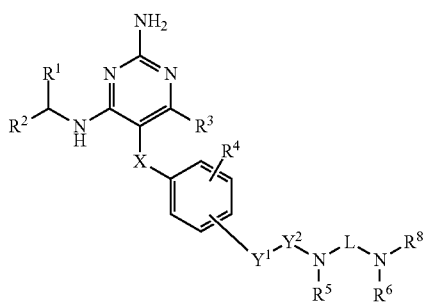

(2)

wherein

X is methylene, oxygen atom, sulfur atom, SO, $SO_2$ or $NR^7$ wherein $R^7$ is hydrogen atom or an alkyl group of 1 to 3 carbon atoms;

R¹ and R² are independently hydrogen atom or a substituted or unsubstituted alkyl group of 1 to 6 carbon atoms, provided that when the alkyl group is substituted, it is substituted with 1 to 4 same or different substituents selected from the group consisting of hydroxy group, halogen atom, and an alkoxy group of 1 to 6 carbon atoms;

R³ is an alkyl group of 1 to 6 carbon atoms, an alkoxy group of 1 to 6 carbon atoms or an alkylthio group of 1 to 6 carbon atoms;

R⁴ is hydrogen atom, halogen atom, hydroxy group, an alkyl group of 1 to 6 carbon atoms, an alkoxy group of 1 to 6 carbon atoms or cyano group;

Y¹ is a single bond, —(CR⁹R¹⁰)$_p$—, —CH=CH—(CR⁹R¹⁰)$_q$—, —C≡C—(CR⁹R¹⁰)$_{q'}$— or —(CR⁹R¹⁰)$_r$—O—(CR⁹'R¹⁰')$_{r'}$— wherein R⁹, R¹⁰, R⁹' and R¹⁰' are independently hydrogen atom or an alkyl group of 1 to 4 carbon atoms;

Y² is a single bond or —C(O)—;

L is a substituted or unsubstituted straight chain alkylene of 2 to 6 carbon atoms or a divalent group derived from 4- to 8-membered cycloalkane, provided that when the straight chain alkylene or the cycloalkane is substituted, it is substituted with 1 to 4 same or different substituents selected from the group consisting of alkyl group of 1 to 5 carbon atoms, hydroxy group and halogen atom, and any one of the methylene group in the straight chain alkylene of L is optionally replaced with carbonyl group;

R⁵ and R⁶ are independently hydrogen atom or a substituted or unsubstituted alkyl group of 1 to 6 carbon atoms, or either R⁵ or R⁶ is bonded to any carbon atom of L to form a 4- to 8-membered nitrogen-containing saturated heterocycle, or R⁵ and R⁶ are taken together to form a substituted or unsubstituted 5- to 8-membered nitrogen-containing saturated heterocycle; provided that when the alkyl group is substituted, it is substituted with same or different 1 to 4 groups selected from the group consisting of hydroxy group and halogen atom; when the 4- to 8-membered nitrogen-containing saturated heterocycle or the 5- to 8-membered nitrogen-containing saturated heterocycle is substituted, it is substituted with same or different 1 to 4 groups selected from the group consisting of methyl group, ethyl group, propyl group, hydroxymethyl group, hydroxyethyl group, carbonyl group, hydroxy group and halogen atom;

p is an integer of 1 to 6;

q and q' are independently an integer of 0 to 4;

r is an integer of 0 to 5, and r' is an integer of 1 to 5, provided that r' is an integer of 2 or more when the sum of r and r' is 5 or less and Y² is a single bond; and R⁸ is hydrogen atom or an amino protecting group.

[20] The compound or a pharmaceutically acceptable salt thereof according to [19] wherein X is methylene;

R¹ is hydrogen atom or an alkyl group of 1 to 3 carbon atoms optionally substituted with hydroxy group;

R² is hydrogen atom or an alkyl group of 1 to 6 carbon atoms;

R³ is an alkyl group of 1 to 3 carbon atoms;

R⁴ is hydrogen atom, halogen atom, hydroxy group, an alkyl group of 1 to 3 carbon atoms or an alkoxy group of 1 to 3 carbon atoms;

Y¹ is a single bond or methylene;

Y² is a single bond or —C(O)—;

L is a straight chain alkylene of 2 or 3 carbon atoms;

$R^5$ and $R^6$ are independently hydrogen atom or an alkyl group of 1 to 3 carbon atoms, or $R^5$ and $R^6$ are taken together to form a substituted or unsubstituted 5- to 8-membered nitrogen-containing saturated heterocycle; provided that when the 5- to 8-membered nitrogen-containing saturated heterocycle is substituted, it is substituted with same or different 1 to 4 groups selected from the group consisting of hydroxy group and halogen atom.

Effect of the Invention

The present invention is able to provide an adjuvant that enhances a specific immune reaction against an antigen useful as a vaccine.

DESCRIPTION OF EMBODIMENTS

Figure 1:
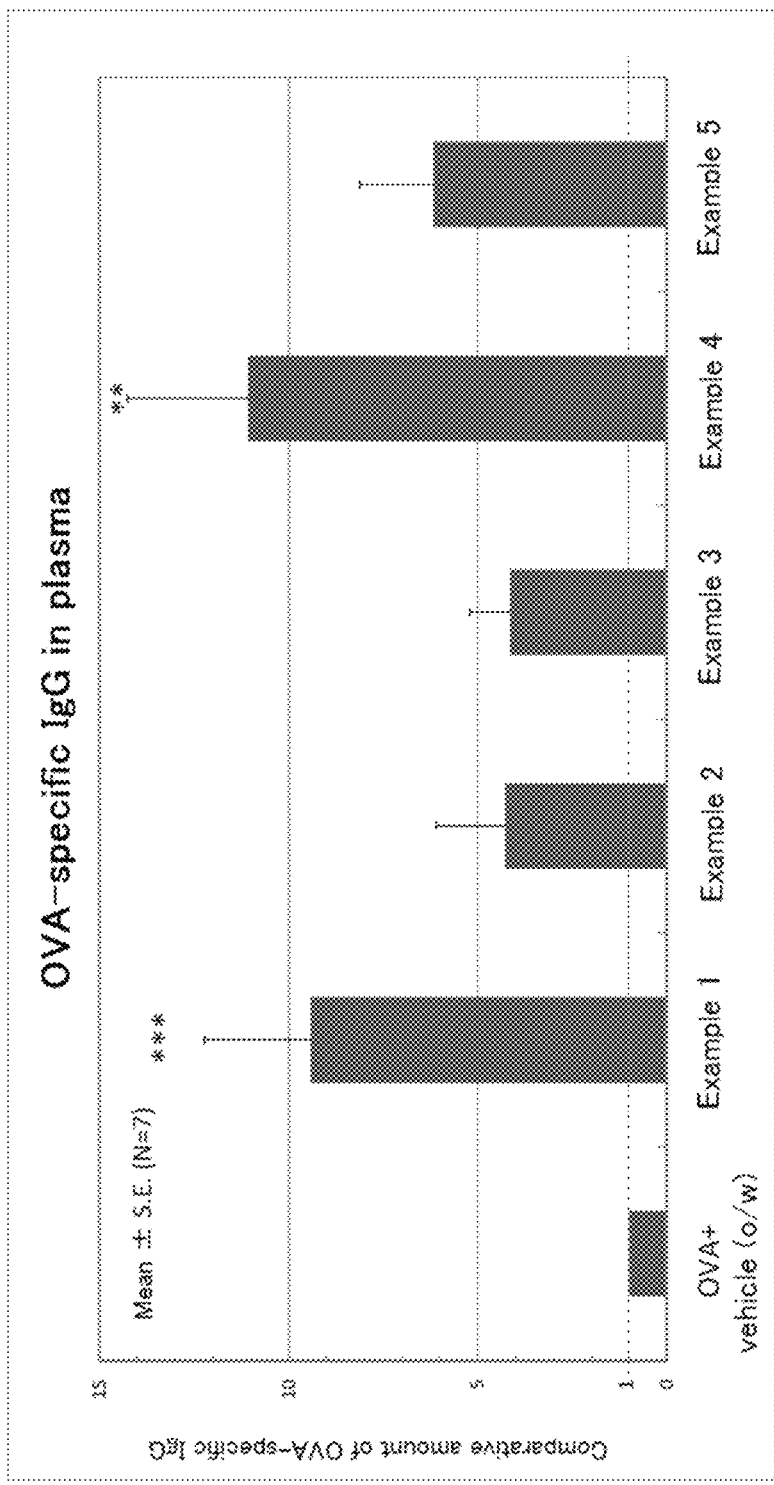
FIG. 1 shows the amount of OVA-specific IgG produced after immunization with OVA in mice which were administered intramuscularly with the compounds of Examples 1 to 5.

In case that a compound of the formula (I) as defined above exists in optically active or racemic forms by virtue of one or more asymmetric carbon atoms, the present disclosure includes in its scope any such optically active or racemic form having a physiological activity as referred to hereinafter. The synthesis of such optically active forms may be carried out by standard techniques of organic chemistry well known in the art, for example, a synthesis from optically active starting materials or a resolution of a racemic mixture. The physiological activity may be evaluated using a standard laboratory technique as referred to hereinafter.

The compound of the formula (I) may exist in an unsolvated or solvated form, such as a hydrate.

Also, the compound of the formula (1) may be deuterated form, wherein one or more $^1H$ are replaced with $^2H$ (D).

The form of the compound of the formula (1) may be, but not limited to, amorphous or exist as a crystal. Crystal polymorphism may be present in a crystalline compound of the formula (1) or a pharmaceutically acceptable salt thereof, and thus, the compound of the present invention includes those in any crystal form.

The term "halogen atom" as used herein includes fluorine atom, chlorine atom, bromine atom, and iodine atom, and preferably, fluorine atom or chlorine atom.

The term "straight chain alkylene" as used herein includes a straight chain alkylene of 1 to 6 carbon atoms. Specific examples of the straight chain alkylene include, but are not limited to, methylene, ethylene, n-propylene and n-butylene.

The term "alkyl group" as used herein includes a straight or branched chain alkyl group of 1 to 6 carbon atoms. Specific examples of the alkyl groups include, but are not limited to, methyl, ethyl, propyl, isopropyl, butyl, isobutyl, and tert-butyl.

The term "cycloalkane" as used herein includes 4 to 8-membered cycloalkanes, specifically, cyclobutane, cyclopentane, cyclohexane, cycloheptane and cyclooctane, and preferably, cyclopentane, cyclohexane or cycloheptane.

The term "divalent group derived from cycloalkane" includes, but not limited to, a divalent group capable of bonding to neighboring atoms on different carbon atoms on the cycloalkane.

The term "alkoxy group" as used herein includes a straight or branched chain alkoxy group of 1 to 6 carbon atoms. Specific examples of alkoxy groups include, but are not limited to, methoxy, ethoxy, propoxy, isopropoxyl, butoxy, isobutoxy, tert-butoxy, pentoxy, and isopentoxy.

The term "4- to 8-membered nitrogen-containing saturated heterocycle" includes 4- to 8-membered nitrogen-containing saturated heterocycle containing 1 to 3 hetero atoms selected from 2 or 3 nitrogen atoms, 0 or 1 oxygen atom and 0 or 1 sulfur atom wherein at least two nitrogen atoms are contained in the ring. Specific examples include azetidine, pyrrolidine, piperidine, perhydroazepine, imidazolidine, piperazine, morpholine, thiomorpholine and perhydro-1,4-diazepine.

The "5- to 8-membered nitrogen-containing saturated heterocycle" may be 5- to 8-membered ones of the aforementioned "4- to 8-membered nitrogen-containing saturated heterocycle".

Examples of the substituent group for the nitrogen-containing saturated heterocycle include preferably methyl group, ethyl group, propyl group, hydroxymethyl group, hydroxyethyl group, carbonyl group, hydroxy group and halogen atom, and more preferably hydroxy group and halogen atom. The nitrogen-containing saturated heterocycle may be substituted with same or different 1 to 4 said substituent groups.

In the formula (1), X represents methylene, oxygen atom, sulfur atom, SO, $SO_2$ or $NR^7$ wherein $R^7$ represents hydrogen atom or an alkyl group of 1 to 3 carbon atoms. $R^7$ preferably represents hydrogen atom or methyl group. X preferably represents methylene.

In the formula (1), $R^1$ preferably represents hydrogen atom or an alkyl group of 1 to 4 carbon atoms. Specific examples of $R^1$ include methyl group, ethyl group, propyl group and butyl group.

In the formula (1), $R^2$ represents hydrogen atom or a substituted or unsubstituted alkyl group of 1 to 4 carbon atoms. When the alkyl group is substituted, specific examples of the substituent group include hydroxy group. Specific examples of $R^2$ include hydrogen atom, methyl group, ethyl group, propyl group, hydroxymethyl group and hydroxyethyl group.

In the formula (1), $R^3$ preferably represents an alkyl group of 1 to 4 carbon atoms, an alkoxy group of 1 to 4 carbon atoms or an alkylthio group of 1 to 4 carbon atoms, more preferably an alkyl group of 1 to 3 carbon atoms or an alkoxy group of 1 to 3 carbon atoms. Specific examples of $R^3$ include methyl group, ethyl group, propyl group or butyl group, and more preferably methyl group.

In the formula (1), examples of $R^4$ include preferably hydrogen atom, an alkyl group of 1 to 3 carbon atoms, an alkoxy group of 1 to 3 carbon atoms, hydroxy or halogen atom, and more preferably hydrogen atom and methoxy group.

In the formula (1), $Y^1$ preferably represents a single bond, $-(CR^9R^{10})_p-$ or $-(CR^9R^{10})_r-O-(CR^{9'}R^{10'})_{r'}-$ wherein $R^9$, $R^{10}$, $R^{9'}$ and $R^{10'}$ are independently hydrogen atom or an alkyl group of 1 to 4 carbon atoms. $R^9$, $R^{10}$, $R^{9'}$ and $R^{10'}$ are preferably independently hydrogen atom or methyl group, more preferably hydrogen atom. More preferably, $Y^1$ is a single bond or $-(CR^9R^{10})_p-$.

In the formula (1), when $Y^1$ is $-(CR^9R^{10})_p-$, p is preferably an integer of 1 to 4, more preferably 1, 2 or 3.

In the formula (1), when $Y^1$ is $-CH=CH-(CR^9R^{10})_q-$ or $-C\equiv C-(CR^9R^{10})_{q'}-$, q and q' are preferably independently an integer of 0 to 3, more preferably 0 or 1.

In the formula (1), when $Y^1$ is $-(CR^9R^{10})_r-O-(CR^9R^{10})_{r'}-$, r is preferably an integer of 0 to 3, r' is preferably 1 to 4. The sum of r and r' is 5 or less, more preferably r is 0 or 1, and r' is 1 or 2.

In the formula (1), when $Y^1$ is a single bond or $-(CR^9R^{10})_p-$, $Y^2$ represents a single bond or $-C(O)-$ (carbonyl).

In a preferred embodiment, $Y^1$ represents a single bond and $Y^2$ represents $-C(O)-$.

In a preferred embodiment, $Y^1$ represents $-(CR^9R^{10})_p-$ and $Y^2$ represents a single bond wherein $R^9$ and $R^{10}$ are preferably independently hydrogen atom or methyl group, more preferably hydrogen atom, and p is preferably an integer of 1 to 4, more preferably 1, 2 or 3.

According to one embodiment of the present invention, L in the formula (1) is a straight chain alkylene of 2 to 4 carbon atoms, preferably straight chain alkylene of 2 or 3 carbon atoms, and more preferably ethylene.

In one embodiment of the present invention, L in the formula (1) represents a divalent group derived from 4- to 8-membered cycloalkane, more preferably a divalent group derived from 5- or 6-membered cycloalkane. Specific examples of the divalent group include the following divalent groups.

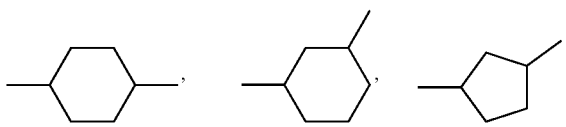

In one embodiment of the present invention, $R^5$ and $R^6$ in the formula (1) represents hydrogen atom or a substituted or unsubstituted alkyl group of 1 to 3 carbon atoms, preferably independently hydrogen atom or an alkyl group of 1 to 3 carbon atoms, more preferably independently hydrogen atom or methyl group, and still more preferably hydrogen atom. When the alkyl group is substituted, it is substituted with 1 to 4 same or different substituents selected from hydroxy group or halogen atom.

In one embodiment of the present invention, either $R^5$ or $R^6$ in the formula (1) may be bonded to any carbon atom of L to form a 4- to 8-membered nitrogen-containing saturated heterocycle, preferably a 4- to 6-membered nitrogen-containing saturated heterocycle. Specific examples of the 4- to 8-membered nitrogen-containing saturated heterocycle formed by $R^5$ in combination with any carbon atom of L include the followings.

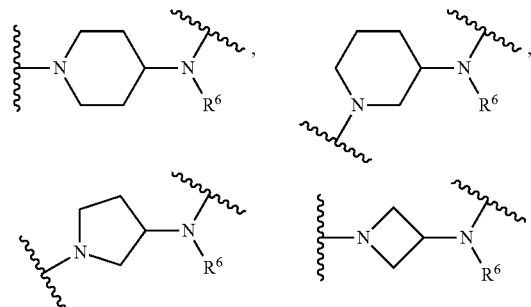

wherein $R^6$ represents hydrogen atom or a substituted or unsubstituted alkyl group of 1 to 6 carbon atoms.

Specific examples of the 4- to 8-membered nitrogen-containing saturated heterocycle formed by $R^6$ in combination with any carbon atom of L include the followings.

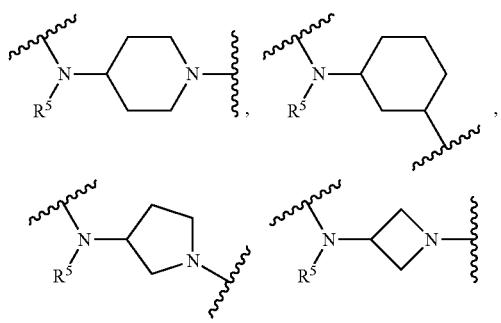

wherein $R^5$ represents hydrogen atom or a substituted or unsubstituted alkyl group of 1 to 6 carbon atoms.

In one embodiment of the present invention, $R^5$ and $R^6$ in the formula (1) may be taken together to form a substituted or unsubstituted 5- to 8-membered nitrogen-containing saturated heterocycle, preferably 5- or 6-membered nitrogen-containing saturated heterocycle. Specific examples of such saturated nitrogen-containing hetero ring include the nitrogen-containing saturated heterocycles of the following formulae:

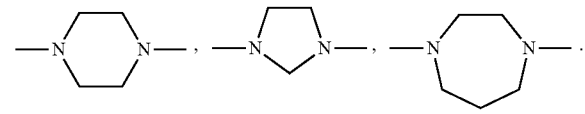

When either $R^5$ or $R^6$ is bonded to any carbon atom of L to form a substituted 4- to 8-membered nitrogen-containing saturated heterocycle or when $R^5$ and $R^6$ are taken together to form a substituted 5- to 8-membered nitrogen-containing saturated heterocycle, the substituent group are preferably same or different 1 to 4 substituents selected from hydroxy group or a halogen atom.

In the formula (1), m preferably represents 1.

In the formula (1), the bonds represented by ====== independently are a single bond or a double bond, preferably all single bonds or all double bonds, more preferably all double bonds.

In a preferred embodiment, the compound of the formula (1) is a compound wherein X represents methylene, $R^1$ represents an alkyl group of 1 to 4 carbon atoms, $R^2$ represents hydrogen atom, an alkyl group of 1 to 3 carbon atoms, or an alkyl group of 1 to 3 carbon atoms substituted with hydroxy group, $R^3$ represents an alkyl group of 1 to 3 carbon atoms or an alkoxy group of 1 to 3 carbon atoms, $R^4$ represents hydrogen atom, halogen atom, hydroxy group, an alkyl group of 1 to 6 carbon atoms or an alkoxy group of 1 to 6 carbon atoms, $Y^1$ represents a single bond or —$(CR^9R^{10})_p$—, $Y^2$ represents —C(O)—, L represents a straight chain alkylene of 2 to 6 carbon atoms, $R^5$ and $R^6$ independently represent hydrogen atom or an alkyl group of 1 to 3 carbon atoms or either $R^5$ or $R^6$ is bonded with any carbon atom of L to form a 4- to 8-membered nitrogen-containing saturated heterocycle or $R^5$ and $R^6$ are taken together to form a substituted or unsubstituted 4- to 8-membered nitrogen-containing saturated heterocycle, m represents 0 or 1, preferably 1, ------ represent all single bonds or all double bonds, or a pharmaceutically acceptable salt thereof.

In a preferred embodiment, the compound of the formula (1) is a compound wherein X represents methylene, $R^1$ represents an alkyl group of 1 to 4 carbon atoms, $R^2$ represents hydrogen atom, an alkyl group of 1 to 3 carbon atoms, or an alkyl group of 1 to 3 carbon atoms substituted with hydroxy group, $R^3$ represents an alkyl group of 1 to 3 carbon atoms or an alkoxy group of 1 to 3 carbon atoms, $R^4$ represents hydrogen atom, halogen atom, hydroxy group, an alkyl group of 1 to 6 carbon atoms or an alkoxy group of 1 to 6 carbon atoms, $Y^1$ represents —$(CR^9R^{10})_p$—

$Y^2$ represents a single bond,

L represents a straight chain alkylene of 2 to 6 carbon atoms, $R^5$ and $R^6$ independently represent hydrogen atom or an alkyl group of 1 to 3 carbon atoms or either $R^5$ or $R^6$ is bonded with any carbon atom of L to form a 4- to 8-membered nitrogen-containing saturated heterocycle or $R^5$ and $R^6$ are taken together to form a substituted or unsubstituted 4- to 8-membered nitrogen-containing saturated heterocycle, m represents 0 or 1, preferably 1, ------ represent all single bonds or all double bonds, or a pharmaceutically acceptable salt thereof.

In a preferred embodiment, the compound of the formula (1) is a compound wherein X represents methylene, $R^1$ represents an alkyl group of 1 to 4 carbon atoms, $R^2$ represents hydrogen atom, an alkyl group of 1 to 3 carbon atoms, or an alkyl group of 1 to 3 carbon atoms substituted with hydroxy group, $R^3$ represents an alkyl group of 1 to 3 carbon atoms or an alkoxy group of 1 to 3 carbon atoms, $R^4$ represents hydrogen atom, halogen atom, hydroxy group, an alkyl group of 1 to 6 carbon atoms or an alkoxy group of 1 to 6 carbon atoms, $Y^1$ represents a single bond and $Y^2$ represents —C(O)—, or $Y^1$ represents —$(CR^9R^{10})_p$— and $Y^2$ represents a single bond, L represents a straight chain alkylene of 2 to 6 carbon atoms, $R^5$ and $R^6$ independently represent hydrogen atom or an alkyl group of 1 to 3 carbon atoms, m represents 0 or 1, preferably 1, ------ represent all single bonds or all double bonds, or a pharmaceutically acceptable salt thereof.

Examples of preferred compounds of the present invention include the following compounds or pharmaceutically acceptable salts thereof:

(4E,8E,12E,16E,20E)-N-{2-[{4-[(2-amino-4-{[1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;

(4E,8E,12E,16E,20E)-1-(4-{4-[(2-amino-4-{[1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one;

(4E,8E,12E,16E,20E)-1-(4-{4-[(2-amino-4-{[1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one;

4-[(2-amino-4-{[1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; and 4-[(2-amino-4-{[1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide.

Alternatively, (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;

(4E,8E,12E,16E,20E)-1-(4-{4-[(2-amino-4-{[(2S)-1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one;

(4E,8E,12E,16E,20E)-1-(4-{4-[(2-amino-4-{[(2S)-1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one;

4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; and 4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide.

The present invention includes a composition comprising a plurality of the above compounds in combination.

Examples of the pharmaceutically acceptable salt of the compound of the formula (1) as used herein include acid addition salts or base addition salts of the compound of the formula (1).

Examples of the acid addition salt include acid addition salts with inorganic or organic acids such as hydrochloric acid, hydrobromic acid, sulfuric acid, trifluoroacetic acid, citric acid and maleic acid. Examples of the base addition salt include alkali metal salts such as sodium salt and potassium salt, alkaline earth metal salts such as calcium salt, and ammonium salt.

The compound of the formula (1) can be produced by the following processes using a known compound as a starting material.

The starting material may be used as a salt. The following processes are merely illustrative, and the compound may be produced by another process appropriately based on the knowledge of one skilled in organic synthesis.

[Process 1 for the Preparation of Compound (1)]

A compound of the formula (1) or a salt thereof can be prepared, for example, by the following process.

phosphoric acid esters such as diethyl cyanophosphate and diphenylphosphoryl azide; carbodiimides such as 1-ethyl-3-(3-diethylaminopropyl)-carbodiimide hydrochloride (WSC.HCl) and dicyclohexylcarbodiimide (DCC); combinations of a disulfide such as 2,2'-dipyridyl disulfide and a phosphine such as triphenylphosphine; phosphorus halides such as N,N'-bis(2-oxo-3-oxazolidinyl)phosphinic chloride (BOPCl); combinations of an azodicarboxylic acid diester such as diethyl azodicarboxylate and a phosphine such as triphenylphosphine; 2-halo-1-lower alkylpyridinium halides such as 2-chloro-1-methylpyridinium iodide; 1,1'-carbonyldiimidazole (CDI); diphenylphosphoryl azide (DPPA); diethylphosphoryl cyanide (DEPC); tetrafluoroborates such

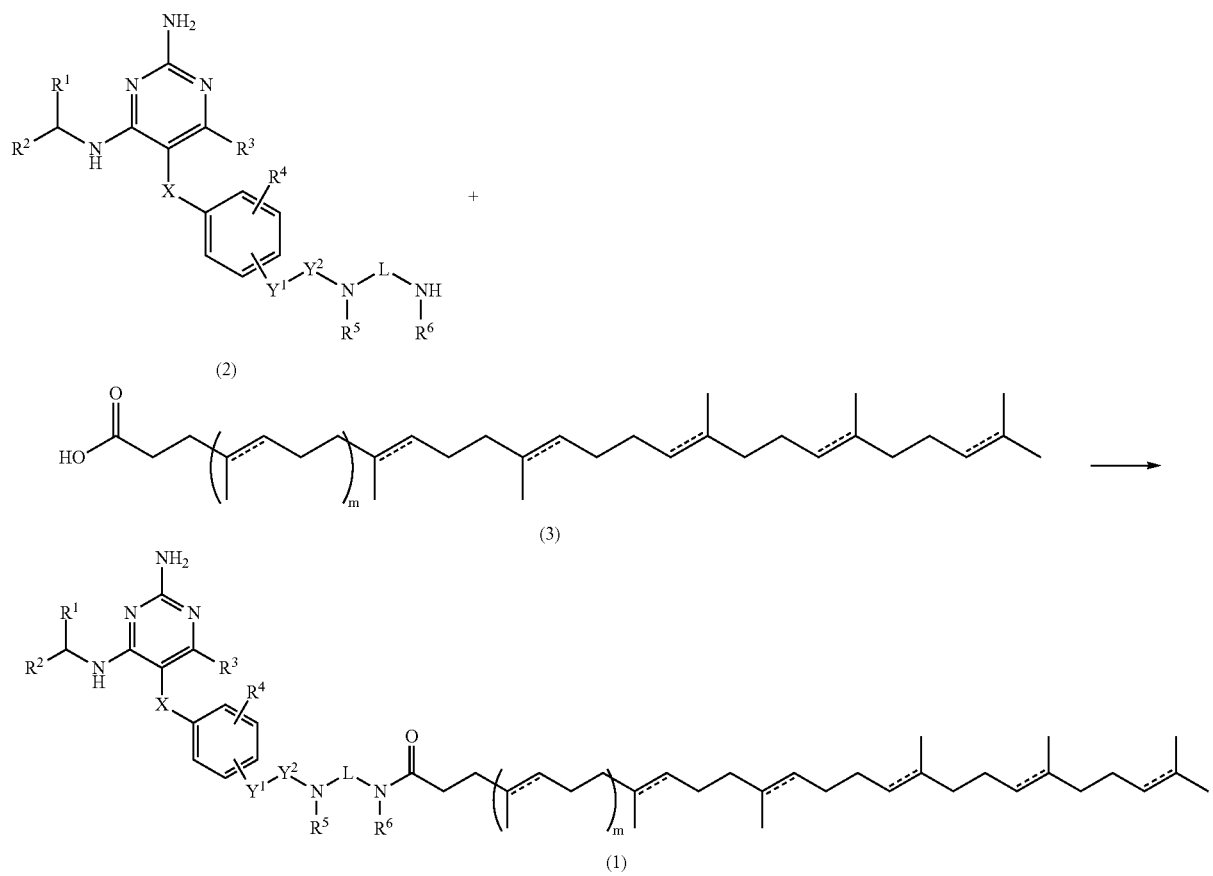

Compound (1) can be prepared by reacting compound (3) with compound (2) in an inert solvent, using a condensing agent, optionally in the presence of a base.

The base is not limited as long as it is used by a person skilled in the art in organic chemical reactions, and examples include organic bases such as N-methyl morpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine and picoline; and inorganic bases such as sodium bicarbonate, potassium bicarbonate, sodium carbonate and potassium carbonate. The base may be used generally in an amount of 0.1 to 100 equivalents, preferably 1 to 5 equivalents, to the compound (3).

The condensing agent may be those described in Experimental Chemistry Course, Vol. 22, edited by The Chemical Society of Japan, Maruzen Co., Ltd., and examples include as 2-(1H-benzotriazole-1-yl)-1,1,3,3-tetramethyluronium tetrafluoroborate (TBTU) and 2-chloro-1,3-dimethylimidazolidinium tetrafluoroborate (CIB); phosphates such as 2-(1H-benzotriazol-1-yl)-1,1,3,3-tetramethyluronium hexafluorophosphate (HBTU), benzotriazol-1-yloxytris(dimethylamino)phosphonium hexafluorophosphate (BOP), benzotriazol-1-yloxytris(pyrrolidino)phosphonium hexafluorophosphate (PYBOP), and 2-(7-aza-1H-benzotriazol-1-yl)-1,1,3,3-tetramethyluronium hexafluorophosphate (HATU).

Examples of the inert solvent include ether solvents such as tetrahydrofuran, diethyl ether, 1,4-dioxane, 1,2-dimethoxyethane; hydrocarbon solvents such as hexane, heptane, toluene, benzene and xylene; halogenated hydrocarbon solvents such as dichloromethane, chloroform and dichloroethane; ketone solvents such as acetone; aprotic solvents such as acetonitrile, N,N'-dimethylformamide, dimethylsulfoxide and hexamethylphosphoramide; and a mixture thereof. The reaction temperature is preferably selected from, but not limited to, the range of about −70° C. to 100° C., more preferably 0° C. to 40° C.

Alternatively, Compound (3) may be converted to an acid halide using a halogenating agent (e.g., 1-chloro-N,N,2-trimethylpropenylamine, phosphorus oxychloride, phosphorus trichloride, thionyl chloride, phosphorus pentachloride) and then reacted with Compound (2) in an inert solvent, optionally in the presence of a base, to obtain Compound (1).

Alternatively, Compound (3) may be converted to an acid halide using a halogenating agent (e.g., 1-chloro-N,N,2-trimethylpropenylamine, phosphorus oxychloride, phosphorus trichloride, thionyl chloride, phosphorus pentachloride) and then reacted with Compound (2) in an inert solvent, optionally in the presence of a base, to obtain Compound (1).

Examples of the inert solvent include ether solvents such as tetrahydrofuran, diethyl ether, 1,4-dioxane, 1,2-dimethoxyethane; hydrocarbon solvents such as hexane, heptane, toluene, benzene and xylene; halogenated hydrocarbon solvents such as dichloromethane, chloroform and dichloroethane; ketone solvents such as methylethyl ketone and acetone; and aprotic solvents such as acetonitrile, N,N'-dimethylformamide, dimethylsulfoxide and hexamethylphosphoramide. Examples of the base include organic bases such as N-methyl morpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine, picoline. The halogenating agent can be used in an amount of 0.1 to 100 equivalents, preferably 0.8 to 3 equivalents, to the compound (3). The reaction temperature is preferably selected from, but not limited to, the range of about −30° C. to 60° C.

Compound (3) can be prepared according to a method well known in the art (see Org. Biomol. Chem. 2011, 9, 4367).

[Process 1 for the Preparation of Compound (2)]

Compound (2a), wherein $Y^2$ in the formula (2) is —C(O)—, or a salt thereof can be prepared, for example, by the following process.

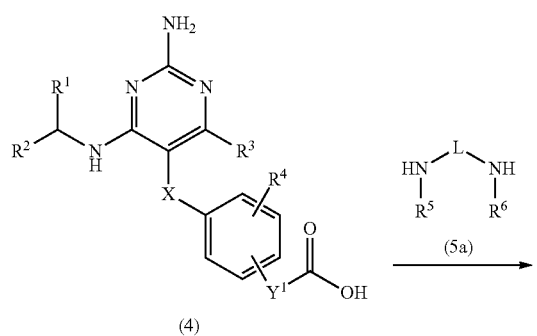

(4)

(5a)

(2a)

wherein X, $R^1$, $R^2$, $R^3$, $R^4$, $R^5$, $R^6$, $Y^1$ and L are as defined above.

Compound (2a) can be synthesized from Compound (4) and Compound (5a) according to a method as described for the preparation of Compound (1).

Compound (4) can be prepared according to a method well known in the art, such as those described in WO 2009/067081 and WO 2010/103885.

[Process 2 for the Preparation of Compound (2)]

Compound (2b), wherein $Y^2$ in the formula (2) is a single bond, or a salt thereof can be prepared, for example, by the following process.

(6)

(5b)

(2b)

wherein X, $R^1$, $R^2$, $R^3$, $R^4$, $R^5$, $R^6$ and L are as defined above, $Y^1$ is —$(CR^9R^{10})_p$—, —CH=CH—$(CR^9R^{10})_q$—, or —C≡C—$(CR^9R^{10})_{q'}$- wherein p, q and q' are as defined above, and
(1) $Q^1$ represents —$Y^1NHR^5$ and $Q^2$ represents CHO; or
(2) $Q^1$ represents —$Y^{1'}$—CHO, wherein $Y^{1'}$ is absent or represents alkylene and —$Y^{1'}$—$(CR^9R^{10})$— corresponds to —$Y^1$—, and $Q^2$ represents —$CH_2NHR^5$.

Compound (2b) can be prepared by coupling Compound (6) and the compound (5b) under a condition for reductive amination well known in the art. Specifically, an aldehyde compound and an amine compound can be reacted in a solvent with a reducing agent, such as sodium triacetoxyborohydride and sodium cyanoborohydride, in the presence or absence of an acid such as acetic acid to prepare Compound (2b).

Compound (6) can be prepared according to a method well known in the art, such as those described in WO2010/133885, WO2012/066335, and WO2012/066336.

[Process 3 for the Preparation of Compound (2)]

Also, Compound (2b) or a salt thereof can be prepared according to the following process.

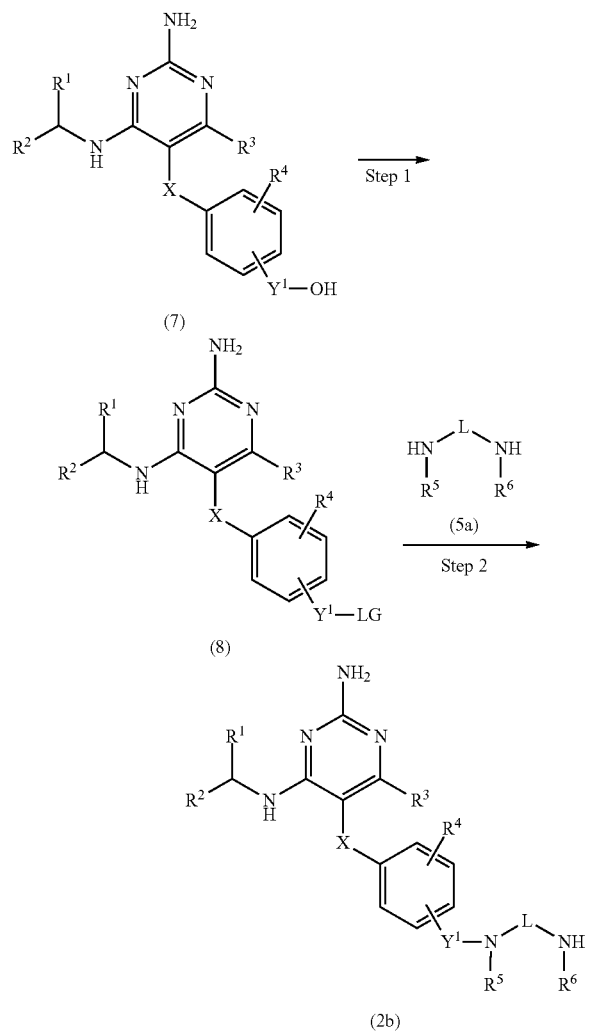

wherein X, $R^1$, $R^2$, $R^3$, $R^4$, $R^5$, $R^6$ and L are as defied above, and $Y^1$ is —$(CR^9R^{10})_p$—, —CH=CH—$(CR^9R^{10})_q$—, —C≡C—$(CR^9R^{10})q'$-, or —$(CR^9R^{10})_r$—O—$(CR^{9'}R^{10'})_{r'}$—, wherein $R^9$, $R^{10}$, $R^{9'}$, $R^{10'}$, p, q, q', r and r' are as defined above, and LG is a leaving group.

Step 1

Compound (7) can be prepared according to a method well known in the art (see WO 2010/133885, WO 2012/066336, etc.). The leaving group LG in Compound (8) is not limited so long as it is well known in the art, and a halogen atom, an alkylsulfonyloxy group, an arylsulfonyloxy group, or the like can be used appropriately.

Compound (8) can be prepared by reacting Compound (7) with methanesulfonyl chloride, p-toluenesulfonyl chloride or the like, in the presence of a base such as triethylamine, diisopropylethylamine, pyridine, dimethylaminopyridine, sodium carbonate, potassium carbonate or the like. The reaction temperature is preferably selected from, but not limited to, the range of about 0° C. to 120° C.

Step 2

Compound (2b) can be prepared by reacting Compound (8) with Compound (5a) in an inert solvent in the presence of a base.

The base is not limited so long as it is used as a base in a usual reaction, and examples include organic bases such as N-methyl morpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine; inorganic bases such as sodium bicarbonate, potassium bicarbonate, sodium carbonate, potassium carbonate, cesium carbonate, sodium hydroxide and sodium hydride. The base may be used generally in an amount of 0.1 to 100 equivalents, preferably 1 to 3 equivalents, to Compound (8).

Examples of the inert solvent include ether solvents such as tetrahydrofuran, diethyl ether, 1,4-dioxane, 1,2-dimethoxyethane; hydrocarbon solvents such as hexane, heptane, toluene, benzene and xylene; aprotic solvents such as acetonitrile, N,N'-dimethylformamide, N-methyl pyrrolidone, dimethylsulfoxide; and a mixture thereof. The reaction temperature is preferably selected from, but not limited to, the range of about 0° C. to 120° C.

[Process 4 for the Preparation of Compound (2)]

Also, Compound (2b) or a salt thereof can be prepared according to the following process.

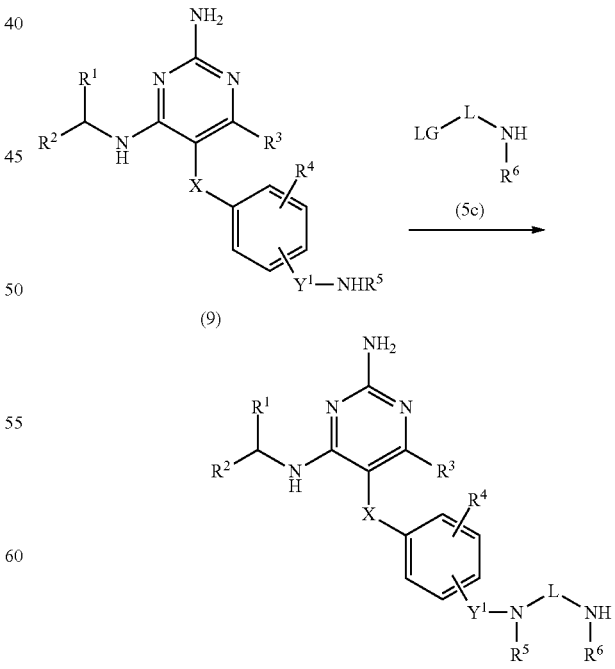

wherein X, R¹, R², R³, R⁴, R⁵ and R⁶ are as defined above, L is substituted or unsubstituted alkylene of 2 to 6 carbon atoms, $Y^1$ is a single bond, —(CR⁹R¹⁰)$_q$—, —CH=CH—(CR⁹R¹⁰)$_q$—, —C≡C—(CR⁹R¹⁰)q'-, or —(CR⁹R¹⁰)$_r$—O—(CR⁹'R¹⁰')$_{r'}$—, wherein R⁹, R¹⁰, R⁹', R¹⁰', q, q', r and r' are as defined above, and LG is a leaving group.

Compound (2b) can be prepared in the similar manner as described in Step 2 of Process 3 for the preparation of Compound (2), using Compound (9) and Compound (5c).

Compound (9) can be prepared according to a method well known in the art, such as those described in WO2010/133885, and WO2012/066336.

[Process 5 for the Preparation of Compound (2)]

Compound (2c) or a salt thereof can be prepared according to the following process.

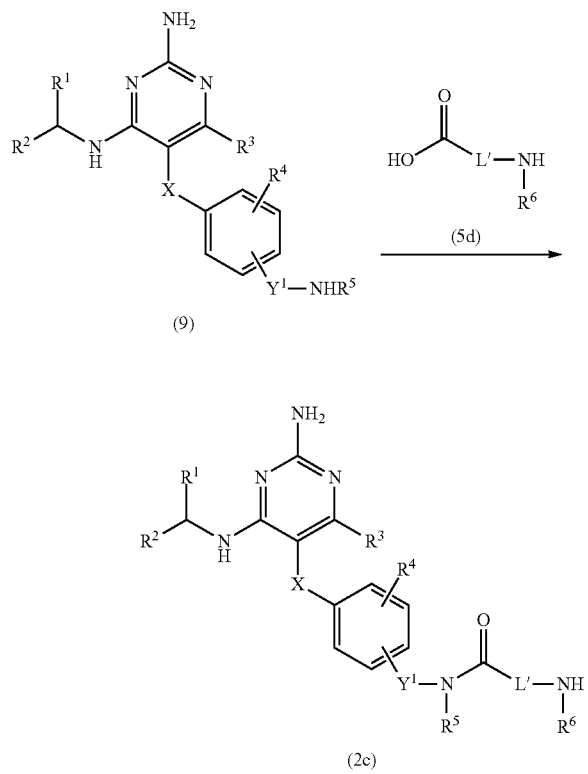

wherein X, R¹, R², R³, R⁴, R⁵ and R⁶ are as defined above, L' is substituted or unsubstituted alkylene of 1 to 5 carbon atoms, $Y^1$ is a single bond, —(CR⁹R¹⁰)$_p$—, —CH=CH—(CR⁹R¹⁰)$_q$—, —C≡C—(CR⁹R¹⁰)q'-, or —(CR⁹R¹⁰)$_r$—O—(CR⁹'R¹⁰')$_{r'}$— wherein R⁹, R¹⁰, R⁹', R¹⁰', p, q, r and r' are as defined above.

Compound (2c) can be prepared as described in the process for the preparation of Compound (1), using Compound (9) and Compound (5d).

The present invention provides intermediates in the processes described above. Examples of such intermediates include compounds of the formula (2):

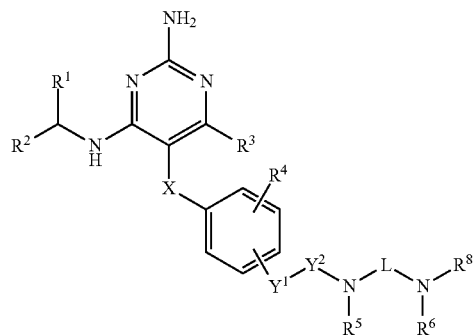

(2)

wherein

X is methylene, oxygen atom, sulfur atom, SO, $SO_2$ or NR⁷ wherein R⁷ is hydrogen atom or an alkyl group of 1 to 3 carbon atoms;

R¹ and R² are independently hydrogen atom or a substituted or unsubstituted alkyl group of 1 to 6 carbon atoms, provided that when the alkyl group is substituted, it is substituted with 1 to 4 same or different substituents selected from the group consisting of hydroxy group, halogen atom, and an alkoxy group of 1 to 6 carbon atoms;

R³ is an alkyl group of 1 to 6 carbon atoms, an alkoxy group of 1 to 6 carbon atoms or an alkylthio group of 1 to 6 carbon atoms;

R⁴ is hydrogen atom, halogen atom, hydroxy group, an alkyl group of 1 to 6 carbon atoms, an alkoxy group of 1 to 6 carbon atoms or cyano group;

$Y^1$ is a single bond, —(CR⁹R¹⁰)$_p$—, —CH=CH—(CR⁹R¹⁰)$_q$—, —C≡C—(CR⁹R¹⁰)$_{q'}$—, or (CR⁹R¹⁰)$_r$—O—(CR⁹'R¹⁰')$_{r'}$— wherein R⁹, R¹⁰, R⁹', and R¹⁰' are independently hydrogen atom or an alkyl group of 1 to 4 carbon atoms;

$Y^2$ is a single bond or —C(O)—;

L is a substituted or unsubstituted straight chain alkylene of 2 to 6 carbon atoms or a divalent group derived from 4- to 8-membered cycloalkane, provided that when the straight chain alkylene or the cycloalkane is substituted, it is substituted with 1 to 4 same or different substituents selected from the group consisting of alkyl group of 1 to 5 carbon atoms, hydroxy group and halogen atom, and any one of the methylene group in the straight chain alkylene of L is optionally replaced with carbonyl group;

R⁵ and R⁶ are independently hydrogen atom or a substituted or unsubstituted alkyl group of 1 to 6 carbon atoms, or either R⁵ or R⁶ is bonded to any carbon atom of L to form a 4- to 8-membered nitrogen-containing saturated heterocycle, or R⁵ and R⁶ are taken together to form a substituted or unsubstituted 5- to 8-membered nitrogen-containing saturated heterocycle; provided that when the alkyl group is substituted, it is substituted with same or different 1 to 4 groups selected from the group consisting of hydroxy group and halogen atom; when the 4- to 8-membered nitrogen-containing saturated heterocycle or the 5- to 8-membered nitrogen-containing saturated heterocycle is substituted, it is substituted with same or different 1 to 4 groups selected from the group consisting of methyl group, ethyl group, propyl group, hydroxymethyl group, hydroxyethyl group, carbonyl group, hydroxy group and halogen atom;

p is an integer of 1 to 6;

q and q' are independently an integer of 0 to 4;

r is an integer of 0 to 5, and r' is an integer of 1 to 5, provided that r' is an integer of 2 or more when the sum of r and r' is 5 or less and $Y^2$ is a single bond; and $R^8$ is hydrogen atom or an amino protecting group, and pharmaceutically acceptable salts thereof.

The protecting group of $R^8$ in the formula (2) may be, but not limited to, a group commonly used as a protecting group for amino group. Specific examples include carbamates such as t-butoxycarbonyl group, benzyloxycarbonyl group and 9-fluorenylmethyloxycarbonyl group; benzyl group; sulfones such as nosyl group; imides such as phthalimide.

In a process of the invention, if a specific functional group, such as hydroxy group or amino group, in a reagent is necessary to be protected, protection/deprotection may be conducted with one or more protecting group at an appropriate step in the process according to a procedure well known in the art.

The protection/deprotection of functional groups is described in J. W. F. McOmie, Ed., "Protective Groups in Organic Chemistry", Plenum Press (1973) and T. W. Greene and P. G. M. Wuts, "Protective Groups in Organic Synthesis," 3rd Edition, Wiley-Interscience (1999).

The present invention provides a pharmaceutical composition comprising a compound of the formula (1) or a pharmaceutically acceptable salt thereof as defined above, in combination with a pharmaceutically acceptable diluent or carrier.

The pharmaceutical composition can be used as an adjuvant for maintaining or enhancing the immunostimulatory activity of the active ingredient having immunostimulatory activity.

That is, the compound of the present invention or a pharmaceutically acceptable salt thereof has an activity of inducing or enhancing an antigen-specific antibody, specifically an antigen-specific IgG, more specifically a Th1 type antigen-specific IgG (e.g., IgG2c).

In addition, the compound of the present invention or a pharmaceutically acceptable salt thereof has an activity of inducing or enhancing CD4-positive (i.e., MHC class 2-restricted) and/or CD8-positive (i.e., MHC Class 1-restricted) T lymphocytes.

Furthermore, the compound of the present invention or a pharmaceutically acceptable salt thereof has an activity of inducing or enhancing MHC-restricted antigen-specific T lymphocytes.

Also, the compound of the present invention or a pharmaceutically acceptable salt thereof has an activity of inducing or enhancing memory T lymphocytes, specifically CD8-positive effector memory T lymphocytes.

In addition, the compound of the present invention or a pharmaceutically acceptable salt thereof, when it is administered to a mammal, is characterized, in that the activity to induce systemic inflammatory mediators, i.e., to raise the concentration of interferon-α, interferon-γ, IL-6, IP-10, or the like, is lower than that of the same dose of the compound without squalene structure.

The pharmaceutical composition may contain an antigen. Examples of the antigen include a tumor antigen protein; a tumor antigen peptide derived from said tumor antigen protein, such as NY-ESO-1, MAGE-3, WT1 and Her2/neu; a hypervariable region of an antibody; and a pathogen-derived antigen such as a protein or a partial peptide thereof derived from a virus or a bacterium. Also, a complex of such antigen and a carrier is included in the scope of the antigen as used herein. Examples of such complex include those wherein an antigen (including, but not limited to, proteins and peptides) are chemically bonded to a protein that serves as a carrier via a linker well known in the art; and those wherein an antigen is contained in a virus-like particle (VLP). Therefore, the compound of the present invention or a pharmaceutically acceptable salt thereof, by using in combination with the above-mentioned antigen, is useful as a drug for the treatment or prevention of cancer, infection with virus or bacteria.

Also, the compound of the present invention or a pharmaceutically acceptable salt thereof can be used as an adjuvant to assist immunostimulation in a treatment for inducing other immunological or immune reaction. Specific Examples of the treatment include ex vivo and in vivo approaches to enhance the immunogenicity of tumor cells of a patient (e.g., transfection with cytokines such as interleukin 2, interleukin 4 or granulocyte macrophage colony stimulating factor), approaches to reduce T cell anergy, approaches using transfected immune cells (e.g., cytokine-transfected dendritic cells), approaches using cytokine-transfected tumor cell lines, approaches to reduce the function of immunosuppressive cells (e.g., regulatory T cells, bone marrow-derived repressed cells and IDO (indoleamine 2,3-dioxygenase)-expressing dendritic cells), and radiation therapy to induce an immune response.

Examples of the administration route of the pharmaceutical composition includes parenteral administration, specifically intravascular (e.g., intravenous), subcutaneous, intradermal, intramuscular, intranasal, and percutaneous administrations.

In one embodiment, the pharmaceutical composition of the present invention may contain a compound of the formula (1) or a pharmaceutically acceptable salt thereof and a pharmaceutically acceptable diluent or carrier.

The dosage form of the pharmaceutical composition of the present invention may be a liquid formulation for injection or nasal drops or a freeze-dried formulation prepared by lyophilizing the liquid formulation.

Examples of the liquid formulation for injection include an emulsion containing an aqueous solution and an oily composition, a liposome, an aqueous solution or suspension wherein an active ingredient and/or a compound of the formula (1) or a pharmaceutically acceptable salt thereof are dissolved or dispersed in water, and an oily solution or suspension wherein an active ingredient and/or a compound of the formula (1) or a pharmaceutically acceptable salt thereof are dissolved or dispersed in oil.

Examples of the liquid formulation for nasal drops include an emulsion containing an aqueous solution and an oily composition, a liposome, an aqueous solution or suspension wherein an active ingredient and/or a compound of the formula (1) or a pharmaceutically acceptable salt thereof are dissolved or dispersed in water.

The aqueous solution, aqueous solution formulation or aqueous suspension formulation may be an aqueous solution or aqueous suspension containing distilled water for injection, and appropriately, a buffer, a pH adjusting agent, a stabilizer, an isotonizing agent or an emulsifying agent.

The oily composition, oily solution formulation or oily suspension formulation may be a composition containing a vegetable oil and fat, animal oil and fat, a hydrocarbon, a fatty acid ester, or the like, more specifically, a composition containing squalene, squalane, or the like.

The emulsion as used herein may be an oil-in-water emulsion or a water-in-oil emulsion. The oil as used in the oil-in-water emulsion is not limited so long as it is capable of dissolving or uniformly dispersing the compound of the formula (1) (or a pharmaceutically acceptable salt thereof), but may be a vegetable oil and fat, an animal oil and fat, a hydrocarbon, a fatty acid ester, or the like, and more specifically, squalene, squalane, or the like. The oil as used in the water-in-oil emulsion is not limited so long as it is capable of dissolving or uniformly dispersing the compound of the formula (1) (or a pharmaceutically acceptable salt thereof), but may be a vegetable oil and fat, an animal oil and fat, a hydrocarbon, a fatty acid ester, or the like.

Specifically, the oil-in-water emulsion may contain 0.1 to 10 wt % of squalene. In one embodiment, the oil-in-water emulsion may contain 0.001 to 1 wt % of a compound of the formula (1) or a pharmaceutically acceptable salt thereof and 1 to 10 wt % of squalene. The oil-in-water emulsion may further comprise one or more surfactants or buffering agents. The surfactant and its amount are not limited so long as they are preferable to maintain a uniform emulsified state, and examples include polysorbates, polyoxyethylene hydrogenated castor oils, polyoxyethylene polyoxypropylene glycols, fatty acid esters of polyalcohols and fatty acid esters, for example, 0.1 to 5 wt % of polysorbate 80, 0.1 to 5 wt % of sorbitan trioleate (e.g., Span 85™). Examples of the buffering agent include phosphate and organic acid salt.

In preparation of a freeze-dried formulation, an excipient may be added as appropriate. The excipient and its amount are not limited so long as they are preferable to form good freeze-dried cake or lyophilized powder, and examples include saccharides, sugar alcohols, amino acids and sodium chloride, for example, 0.1 to 20% mannitol.

The pharmaceutical composition of the present invention may further contain other additives, and examples of such additives include surfactants, antioxidants, preservatives, and soothing agents.

The compound of the formula (1) or a pharmaceutically acceptable salt thereof may be administered simultaneously with or at any interval before or after the antigenic substance (immunogen) in a unit dose ranging from generally 5 to 5000 mg/m$^2$ of body surface area, i.e., about 0.1 ng/kg to 100 mg/kg, which provides a prophylactically or therapeutically effective dose. The unit dosage form for injections, tablets or capsules generally contains, for example, 1 ng to 250 mg of active ingredient, and preferably, used at a dose ranging from 1 ng to 50 mg/kg per day. However, the daily dose may vary depending on the host to be treated, the route of administration and the severity of the disease being treated. Thus, the optimal dose can be determined by a practitioner who treats individual patient or warm-blooded animal.

The term "treatment" as used herein means alleviating some or all of the symptoms of disease, in whole or in part, or preventing or delaying the progression of disease.

The term "prevention" as used herein means primary prevention of disease (prevention of onset of disease) or secondary prevention (prevention of relapse in a patient whose symptom has been alleviated or disease has been cured after the onset of the disease, prevention of recurrence).

Since the compound of the present invention or its pharmaceutically acceptable salt has an immune adjuvant activity in vitro or in vivo, it is useful as a vaccine adjuvant for maintaining or enhancing the immunogenicity of the antigen.

The compound of the present invention or a pharmaceutically acceptable salt thereof can be used for maintaining or enhancing the effect of an immuno-stimulating substance (immunostimulatory substance) which is an agent for treating or preventing a disease, i.e., a substance inducing an antigen-specific immune reaction.

A pharmaceutical composition comprising a compound of the present invention or a pharmaceutically acceptable salt thereof and a substance enhancing an antigen-specific immune reaction (also referred to as an antigen) is also an embodiment of the present invention. The antigen may be, but not limited to, an antigen protein, an antigen peptide (partial peptide) derived from said antigen protein, or a complex thereof with a carrier.

In a specific embodiment of the invention, a compound of the invention or a pharmaceutically acceptable salt thereof can be administered in combination with a tumor antigen protein or a tumor antigen peptide for cancer immunotherapy to treat or prevent cancer. Examples of the cancer include common cancers such as bladder cancer, head and neck cancer, prostate cancer, breast cancer, lung cancer, ovarian cancer, pancreatic cancer, cancer of intestine and colon, stomach cancer, skin cancer and brain cancer; malignant diseases (Hodgkin's lymphoma and non-Hodgkin's lymphoma, etc.) that affect bone marrow (including leukemia) and lymphoproliferative system. The treatment or prevention of cancer as used herein may be prevention of metastatic disease and tumor recurrence, and prevention and treatment of paraneoplastic syndrome.

Examples of the antigen include, but not limited to, MAGE (Science, 254: p 1643 (1991)), gp 100 (J. Exp. Med., 179: p 1005 (1994)), MART-1 (Proc. Natl. Acad. Sci. USA, 91: p 3515 (1994)), tyrosinase (J. Exp. Med., 178: p 489 (1993)), MAGE related proteins (J. Exp. Med., 179: p 921 (1994)), β-catenin (J. Exp. Med., 183: p 1185 (1996)), CDK4 (Science, 269: p 1281 (1995)), HER2/neu (J. Exp. Med., 181: p 2109 (1995)), mutant p53 (Proc. Natl. Acad. Sci. USA, 93: p 14704(1996)), CEA (J. Natl. Cancer. Inst., 87: p 982 (1995)), PSA (J. Natl. Cancer. Inst., 89: p 293 (1997)), WT1 (Proc. Natl. Acad. Sci. USA, 101: p 13885 (2004)), HPV-derived antigen (J. Immunol., 154: p 5934 (1995)), and EBV-derived antigen (Int. Immunol., 7: p 653 (1995)).

Examples of the tumor antigen peptide derived from the cancer antigen include, but not limited to, MAGEA3 peptide 168-176 (Coulie P G et al., Immunol. Rev. 188: 33 (2002)), gp100 peptide 209-217 (Rosenberg S A et al., Nat. Med. 4: 321 (1998)), gp100 peptide 280-288 (Phan G Q et al., Proc. Natl. Acad. Sci. USA 100: 8372 (2003)), Melan-A peptide 27-35 (Cormier J N et al., Cancer J. Sci. Am. 3: 37 (1997)), Melan-A peptide 26-35, Tyrosinase peptide 1-9, Tyrosinase peptide 368-376, gp100 peptide 280-288, gp100 peptide 457-466 (Jager E et al., Int. J. Cancer 67: 54 (1996)), HER-2 peptide 369-384, HER-2 peptide 688-703, HER-2 peptide 971-984 (Knutson K L et al., J. Clin. Invest. 107: 477 (2001)), and MAGE-A12 peptide 170-178 (Bettinotti M P et al., Int. J. Cancer 105: 210 (2003)).

In addition, the compound of the present invention or its pharmaceutically acceptable salt, by administering in combination with an active ingredient of a vaccine for preventing infectious diseases, can prevent various infectious diseases such as genital wart, common wart, plantar wart, hepatitis B, hepatitis C, herpes simplex virus, molluscum contagiosum, smallpox, human immunodeficiency virus (HIV), human papilloma virus (HPV), RS virus, norovirus, cytomegalovirus (CMV), varicella zoster virus (VZV), rhinovirus, adenovirus, coronavirus, influenza, and parainfluenza; bacterial diseases such as tuberculosis, *Mycobacterium avium*, and Hansen's disease; infections such as mycosis, *Chlamydia, Candida, Aspergillus*, cryptococcal meningitis, *Pneumocystis carini*, cryptosporidiosis, histoplasmosis, toxoplasmosis, malaria, Trypanosoma infection, and leishmaniasis. Examples of the active ingredient of the vaccine for preventing infectious include, but not limited to, substances derived from microorganisms/pathogens including bacteria, fungi, protozoa, and viruses which cause infectious diseases, such as antigenic protein, antigen peptide (partial peptide) from said antigenic protein, polysaccharide, lipid, and a combination thereof or a combination of the substance derived from said microorganisms/pathogens and a carrier.

Examples of the viral antigenic peptide derived from the viral antigen include, but are not limited to, influenza matrix protein peptide 58-66 (Jager E et al., Int. J. Cancer 67: 54 (1996)), HPV16 E7 peptide 86-93 (van Driel W J et al., Eur. J. Cancer 35:946 (1999)), HPV E7 peptide 12-20 (Scheibenbogen C et al., J. Immunother 23: 275 (2000)), HPV16 E7 peptide 11-20 (Smith J W I et al., J. Clin. Oncol. 21: 1562 (2003)), HSV2 gD (Berman P W et al., Science 227: 1490 (1985)), CMV gB (Frey S E et al., Infect Dis. 180: 1700 (1999), Gonczol E. et al., Exp. Opin. Biol. Ther. 1: 401 (2001)), and CMV pp65 (Rosa C L et al., Blood 100: 3681 (2002), Gonczol E. et al., Exp. Opin. Biol. Ther. 1: 401 (2001)).

The carrier as used herein is a substance, such as protein and lipid, to which an antigenic protein or an antigenic peptide is bonded chemically and/or physically, and examples include, but are not limited to, CRM 197 (Vaccine. 2013 Oct. 1; 31(42):4827-33), KLH (Cancer Immunol Immunother. 2003 October; 52(10):608-16), virus-like particles (PLoS ONE 5(3): e9809) and liposomes (J Liposome Res. 2004; 14(3-4):175-89).

The antigenic protein may be prepared by cloning cDNA, which encodes the antigenic protein, and expression in a host cell, according to a textbook such as Molecular Cloning 2nd ed., Cold Spring Harbor Laboratory Press (1989).

The synthesis of the antigenic peptide can be carried out according to a method generally used in peptide chemistry, for example, as described in literatures (Peptide Synthesis, Interscience, New York, 1966; The Proteins, Vol. 2, Academic Press Inc., New York, 1976).

The present invention further provides a kit comprising:
a) a compound of the formula (1), or a pharmaceutically acceptable salt thereof;
b) an antigen; and
c) a container or device to contain a unit dosage form of a) and b) in combination or separately.

The antigen is not limited so long as it is an antigen that may be used as an active ingredient of vaccines, and examples include antigenic proteins as mentioned above, antigenic peptides (partial peptides) derived from such antigenic proteins, and a complex thereof with a carrier.

In one embodiment of the present invention, there is provided a use of a compound of the formula (1), or a pharmaceutically acceptable salt thereof, for the manufacture of a vaccine adjuvant.

In one embodiment of the present invention, there is provided a use of a compound of the formula (I) as defined above, or a pharmaceutically acceptable salt thereof, as a vaccine adjuvant in the manufacture of a vaccine for the treatment of a disease or condition.

One embodiment of the present invention provides a method for the treatment, prevention of or prevention of the progress of the diseases, comprising a step of administering a compound of the formula (I) as defined above, or a pharmaceutically acceptable salt thereof, together with an antigen, to a patient.

The present invention will be further described with reference to the following examples which should not be regarded as limiting in any respect.

EXAMPLES

THF: tetrahydrofuran
EtOAc: ethyl acetate
NMP: N-methylpyrrolidinone
TEA: triethylamine
The measurement conditions for high performance liquid chromatography mass spectrometry (LCMS) were as follows. The observed MS (m/z) values were shown with respect to M+H.
MS detector: LCMS-IT-TOF
HPLC: Shimadzu Nexera X2 LC 30AD
Column: Kinetex 1.7μ C18 100A New column 50×2.1 mm
Flow rate: 1.2 ml/min
Measurement wavelength: 254 nm
Mobile phase: Solution A: 0.1% aqueous formic acid solution
Solution B: acetonitrile
Time program:
Step time (min)

| 1 | 0.01-1.40 | Solution A:Solution B = 90:10 to 5:95 |
| 2 | 1.40-1.60 | Solution A:Solution B = 5:95 |
| 3 | 1.61-2.00 | Solution A:Solution B = 99:1 |

Example 1

(4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide

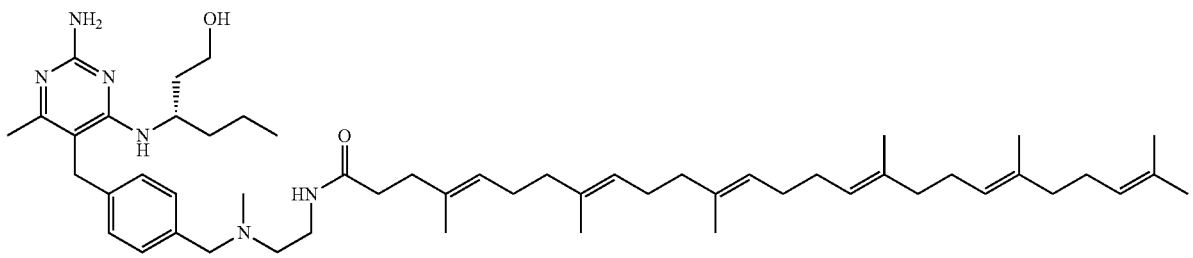 [SMILES: CCC[C@@H](CCO)Nc1nc(N)nc(C)c1Cc1ccc(CN(C)CCNC(=O)CC/C(C)=C/CC/C(C)=C/CC/C(C)=C/CC/C=C(\C)CC/C=C(\C)CCC=C(C)C)cc1]

Step 1

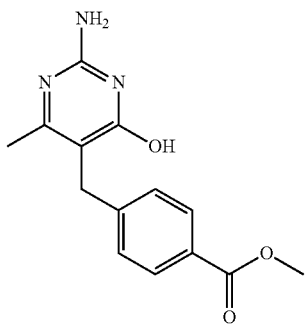

Methyl 4-2-(ethoxycarbonyl)-3-oxobutyl)benzoate (3.56 g, 12.8 mmol) and guanidine carbonate (4.61 g, 25.6 mmol) were dissolved in methanol (23 ml), and the mixture was heated to reflux with stirring for 7 hour. After cooling the reaction mixture, water (30 ml) and acetic acid (0.660 ml, 11.5 mmcl) were added. The precipitated solid was collected by filtration. The solid was suspended in THF and heated to reflux with stirring for one hour. After cooling, the solid was collected by filtration, washed with THF and dried to obtain the desired product (1.62 g, 46%).

$^1$H-NMR (400 MHz, DMSO-d$^6$) δ2.00 (3H, s), 3.71 (2H, s), 3.82 (3H, s), 6.35 (1H, br), 7.31 (2H, d, J=8.3 Hz), 7.84 (2H, d, J=8.3 Hz).

Step 2

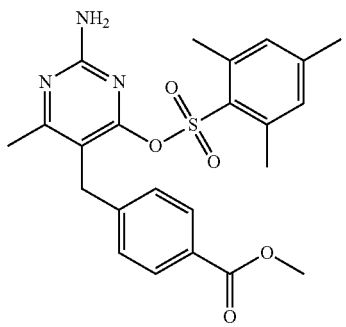

The compound obtained in Step 1 (1.62 g, 5.93 mmol) and N,N,N',N'-tetramethyl-1,3-propanediamine (1.41 ml, 8.89 mmol) were suspended in THF (24 ml), and 2-mesitylene-sulfonyl chloride (1.94 g, 8.89 mmol) was added. The mixture was stirred at room temperature for 20 hours. Water was added to the mixture. The mixture was extracted with ethyl acetate. The organic layer was washed with brine, dried over anhydrous sodium sulfate, filtered, and concentrated under reduced pressure. The obtained solid was washed with ether, and with hexane, and dried to obtain the desired product (2.69 g, 99.6%).

$^1$H-NMR (400 MHz, DMSO-d$^6$) δ2.20 (3H, s), 2.29 (3H, s), 2.48 (6H, s), 3.84 (3H, s), 3.88 (2H, s), 6.35 (1H, br), 7.08 (2H, s), 7.19 (2H, d, J=8.3 Hz), 7.85 (2H, d, J=8.3 Hz).

Step 3

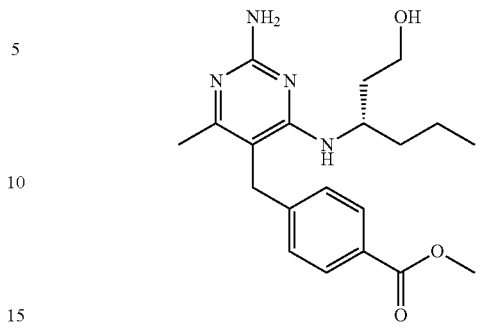

Methyl 4-((2-amino-4-((mesitylsulfonyl)oxy)-6-methylpyrimidin-5-yl)methyl)benzoate (3.6 g, 8.0 mmol) was dissolved in propionitrile (80 ml). (S)-(+)-3-amino-1-hexanol (5.6 g, 48 mmol) and trifluoroacetic acid (1.2 ml, 16 mmol) were added, and the mixture was heated to 110° C. After stirring for 36 hours, the mixture was cooled to room temperature and concentrated under reduced pressure. The residue was purified on silica gel column (ethyl acetate:methanol=20:1 to 5:1) to obtain the desired product (2.1 g, 71%).

$^1$H-NMR (CDCl$_3$) δ 0.73 (t, J=7.2 Hz, 3H), 0.90-1.76 (m, 6H), 2.41 (s, 3H), 3.49-3.61 (m, 2H), 3.69-3.87 (m, 2H), 3.90 (s, 3H), 4.24 (m, 1H), 7.17 (d, J=8.0 Hz, 2H), 7.98 (d, J=8.0 Hz, 2H).

Step 4

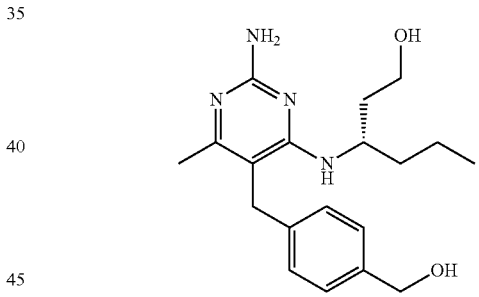

(S)-Methyl 4-((2-amino-4-((1-hydroxyhexan-3-yl)amino)-6-methylpyrimidin-5-yl)methyl)benzoate] (2.1 g, 5.6 mmol) was dissolved in tetrahydrofuran (56 mL)/methanol (5.6 mL). Lithium borohydride (3M in tetrahydrofuran, 5.6 mL, 17 mmol) was added, and the mixture was heated to 60° C. After stirring for 2 hours, lithium borohydride (3M in tetrahydrofuran, 5.6 mL, 17 mmol) was added, and the mixture was further stirred at 60° C. for 2 hours. After cooling to 0° C., 4N hydrochloric acid (30 mL) was added. The mixture was stirred at room temperature for 1 hour, neutralized with aqueous sodium hydrogen carbonate solution, and then extracted with ethyl acetate. The organic layer was washed with brine, dried over magnesium sulfate, and concentrated under reduced pressure to obtain a crude product (1.2 g).

$^1$H-NMR (CD$_3$OD) δ 0.78 (t, J=7.2 Hz, 3H), 1.03-1.76 (m, 6H), 2.18 (s, 3H), 3.41-3.48 (m, 2H), 3.76-3.88 (m, 2H), 4.23 (m, 1H), 4.55 (s, 2H), 7.11 (d, J=8.0 Hz, 2H), 7.26 (d, J=8.0 Hz, 2H).

Step 5

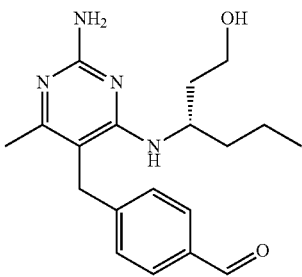 [SMILES: CCC[C@@H](CCO)Nc1nc(N)nc(C)c1Cc1ccc(C=O)cc1]

(S)-3-((2-Amino-5-(4-(hydroxymethyl)benzyl)-6-methylpyrimidin-4-yl)amino)hexan-1-ol (1.2 g, 3.5 mmol) was dissolved in chloroform (35 mL)/methanol (3.5 mL), and manganese dioxide (3.1 g, 35 mmol) was added. The mixture was stirred overnight and filtered through celite. The filtrate was concentrated under reduced pressure. The residue was purified on silica gel column (chloroform:methanol=99:1 to 4:1) to obtain the desired product (0.72 g, 37% in 2 Steps).

$^1$H-NMR (CD$_3$OD) δ 0.70 (t, J=7.2 Hz, 3H), 1.05-1.77 (m, 6H), 2.20 (s, 3H), 3.42-3.50 (m, 2H), 3.90-4.03 (m, 2H), 4.32 (m, 1H), 7.35 (d, J=8.0 Hz, 2H), 7.84 (d, J=8.0 Hz, 2H), 9.93 (s, 1H).

Step 6

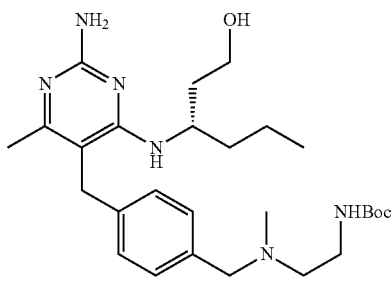 [SMILES: CCC[C@@H](CCO)Nc1nc(N)nc(C)c1Cc1ccc(CN(C)CCNC(=O)OC(C)(C)C)cc1]

(S)-4-((2-Amino-4-((1-hydroxyhexan-3-yl)amino)-6-methylpyrimidin-5-yl)methyl)benzaldehyde (0.28 g, 0.82 mmol) was dissolved in chloroform (8 mL). t-Butyl (2-(methylamino)ethyl)carbamate (0.29 g, 1.6 mmol), acetic acid (0.23 mL, 4.1 mmol) and sodium triacetoxyborohydride (0.52 g, 2.5 mmol) were added. The mixture was stirred overnight at room temperature. Water was added, and the mixture was extracted with ethyl acetate. The organic layer was washed with brine, dried over magnesium sulfate, concentrated under reduced pressure. The residue was purified on amino silica gel column (ethyl acetate:methanol=99:1 to 95:5) to obtain a crude product (0.23 g, 56%).

$^1$H-NMR (CDCl$_3$) δ 0.66 (t, J=7.2 Hz, 3H), 0.91-1.77 (m, 6H), 1.40 (s, 9H), 2.12 (s, 3H), 2.26 (s, 3H), 2.39-2.44 (m, 2H), 3.15-3.46 (m, 4H), 3.43 (s, 2H), 3.61-3.86 (m, 2H), 4.05 (m, 1H), 4.67-4.77 (br, 2H), 4.91-5.01 (br, 1H), 7.05 (d, J=8.0 Hz, 2H), 7.18 (d, J=8.0 Hz, 2H).

Step 7

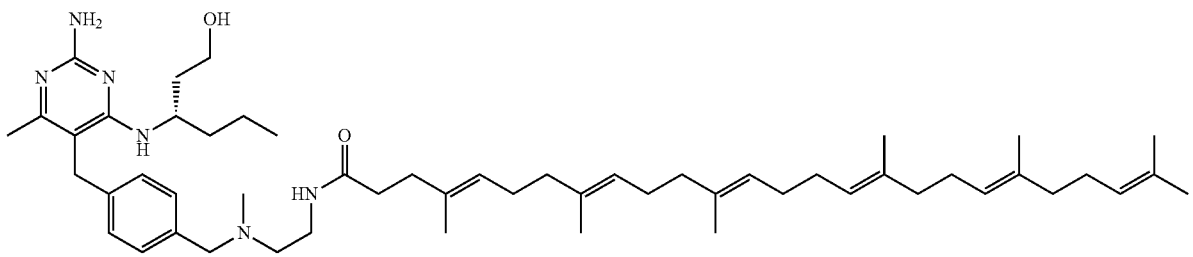 [SMILES: CCC[C@@H](CCO)Nc1nc(N)nc(C)c1Cc1ccc(CN(C)CCNC(=O)CC/C(C)=C/CC/C(C)=C/CC/C(C)=C/CC/C=C(\C)CC/C=C(\C)CCC=C(C)C)cc1]

(S)-Butyl (2-((4-((2-amino-4-((1-hydroxyhexan-3-yl)amino)-6-methylpyrimidin-5-yl)methyl)benzyl)(methyl)amino)ethyl)carbamate (0.150 g, 0.29 mmol) was dissolved in chloroform (4 mL). Hydrogen chloride (4M in cyclopentyl methyl ether, 2.2 ml, 8.80 mmol) was added. The mixture was stirred at room temperature for 1 hour and then concentrated under reduced pressure. (4E,8E,12E,16E,20E)-4,8,12,17,21,25-Hexamethylhexacosa-4,8,12,16,20,24-hexaenoic acid (123 mg, 0.262 mmol), 1-[bis(dimethylamino)methylene]-1H-1,2,3-triazolo[4,5-b]pyridin-1-ium 3-oxide hexafluorophosphate (150 mg, 0.393 mmol) and N,N-diisopropylethylamine (0.137 ml, 0.787 mmol) were dissolved in N,N-dimethyl formamide (3 ml), and the mixture was stirred for 5 minutes. The crude product was dissolved in N,N-dimethyl formamide (3 ml) and added to the mixture. The mixture was stirred overnight at room temperature. Water was added, and the mixture was extracted with ethyl acetate. The organic layer was washed with brine, dried over magnesium sulfate, and concentrated under reduced pressure. The residue was purified on amino silica gel column (chloroform:methanol=99:1 to 90:10) to obtain the desired product (80 mg, 32%).

$^1$H-NMR (CDCl$_3$) δ 0.71 (t, J=7.2 Hz, 3H), 0.92-1.83 (m, 27H), 1.95-2.08 (m, 20H), 2.18-2.32 (m, 10H), 2.46 (t, J=6.0 Hz, 2H), 3.28-3.43 (m, 4H), 3.46 (s, 2H), 3.64-3.81 (m, 2H), 4.10 (m, 1H), 4.48-4.58 (br, 2H), 5.06-5.17 (m, 6H), 5.94-6.04 (br, 1H), 7.06 (d, J=8.0 Hz, 2H), 7.20 (d, J=8.0 Hz, 2H). ESI: [M+H]$^+$ 852.6

Example 2

(4E,8E,12E,16E,20E)-1-(4-{4-[(2-amino-4-{[(2S)-1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one

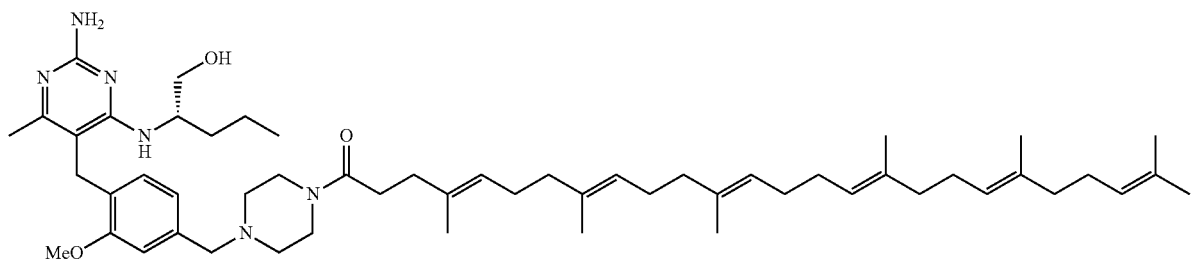 [SMILES: CCC[C@@H](CO)Nc1nc(N)nc(C)c1Cc1ccc(CN2CCN(C(=O)CC/C(C)=C/CC/C(C)=C/CC/C(C)=C/CC/C=C(\C)CC/C=C(\C)CCC=C(C)C)CC2)cc1OC]

The desired product (96 mg, 23% in 2 Steps) was obtained in the similar manner as Step 6 and Step 7 of Example 1, using known compound (S)-4-((2-amino-4-((1-hydroxypentan-2-yl)amino)-6-methylpyrimidin-5-yl)methyl)-3-methoxybenzaldehyde (0.10 g, 0.28 mmol), t-butyl piperazin-1-carboxylate (0.13 g, 0.71 mmol) and (4E,8E,12E,16E,20E)-4,8,12,17,21,25-hexamethylhexacosa-4,8,12,16,20,24-hexaenoic acid (72 mg, 0.15 mmol).
$^1$H-NMR (CDCl$_3$) δ 0.77 (t, J=7.2 Hz, 3H), 1.00-1.44 (m, 4H), 1.57-1.65 (m, 21H), 1.88-2.04 (m, 20H), 2.23-2.38 (m, 11H), 3.38-3.74 (m, 6H), 3.44 (s, 2H), 3.67 (s, 2H), 3.88 (s, 3H), 4.00 (m, 1H), 4.77-4.87 (br, 2H), 5.03-5.11 (m, 6H), 6.79 (d, J=8.0 Hz, 1H), 6.86 (s, 1H), 6.89 (d, J=8.0 Hz, 1H).
ESI: [M+H]$^+$ 879.6

Example 3

(4E,8E,12E,16E,20E)-1-(4-{4-[(2-amino-4-{[(2S)-1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one

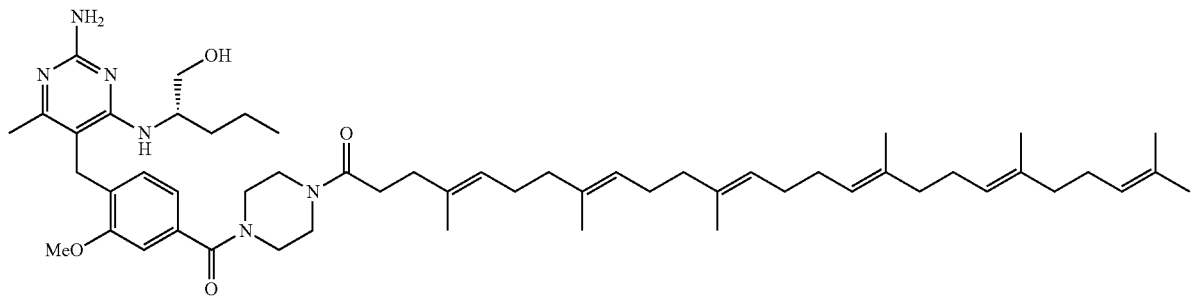 [SMILES: CCC[C@@H](CO)Nc1nc(N)nc(C)c1Cc1ccc(C(=O)N2CCN(C(=O)CC/C(C)=C/CC/C(C)=C/CC/C(C)=C/CC/C=C(\C)CC/C=C(\C)CCC=C(C)C)CC2)cc1OC]

Step 1

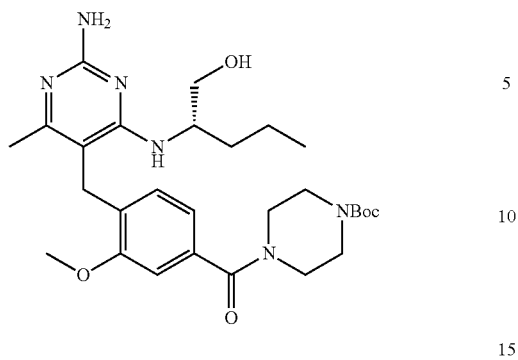

(S)-4-((2-Amino-4-((1-hydroxypentan-2-yl)amino)-6-methylpyrimidin-5-yl)methyl)-3-methoxybenzoic acid (190 mg, 0.507 mmol), which was prepared as described in WO2012/066336, and 1-BOC-piperazine (142 mg, 0.761 mmol) were dissolved in N,N-diethylformamide (5 ml). 1-[Bis(dimethylamino)methylene]-1H-1,2,3-triazolo[4,5-b]pyridinium 3-oxide hexafluorophosphate (289 mg, 0.761 mmol) and N,N-diisopropylethylamine (197 mg, 1.52 mmol) were added, and the mixture was stirred at room temperature for 10 hours. Water was added to the mixture, and the mixture was extracted with chloroform. The organic layer was dried over anhydrous sodium sulfate, filtered, and concentrated under reduced pressure. The resulting residue was purified on silica gel column chromatography (ethyl acetate/methanol=20/1 to 5/1) to obtain the desired product (202 mg, 73%) as colorless amorphous.
MS (ESI+): [M+H]$^+$ 543.4

Step 2

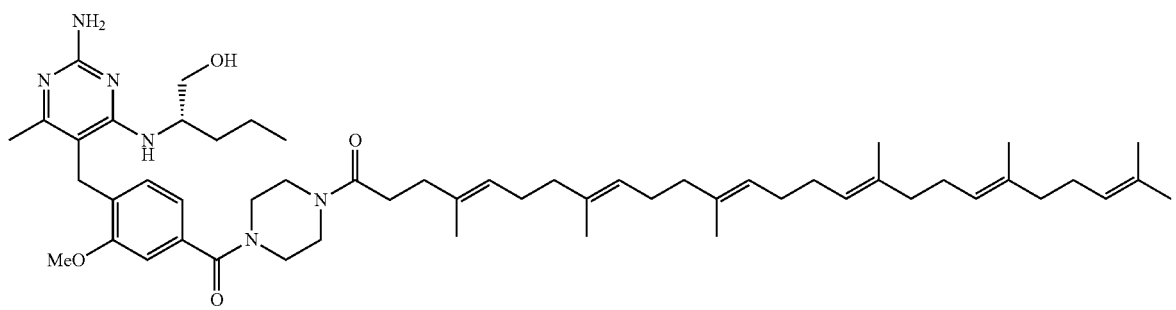 [SMILES: CCC[C@@H](CO)Nc1nc(N)nc(C)c1Cc1ccc(C(=O)N2CCN(C(=O)CC/C(C)=C/CC/C(C)=C/CC/C(C)=C/CC/C=C(\C)CC/C=C(\C)CCC=C(C)C)CC2)cc1OC]

(S)-tert-Butyl 4-(4-((2-amino-4-((1-hydroxypentan-2-yl)amino)-6-methylpyrimidin-5-yl)methyl)-3-methoxybenzoyl)piperazin-1-carboxylate (200 mg, 0.369 mmol) was dissolved in chloroform (3.0 ml). 4M Hydrochloric acid-cyclopentyl methyl ether solution (3 ml, 12.0 mmol) was added, and the mixture was stirred at room temperature for 1 hour. Toluene was added to the reaction mixture, and the mixture was concentrated under reduced pressure. The residue was added to the solution of (4E,8E,12E,16E,20E)-4,8,12,17,21,25-hexamethylhexacosa-4,8,12,16,20,24-hexaenoic acid (166 mg, 0.355 mmol), 1-[bis(dimethylamino)methylene]-1H-1,2,3-triazolo[4,5-b]pyridinium 3-oxide hexafluorophosphate (202 mg, 0.532 mmol) and N,N-diisopropyl ethyl amine (0.185 ml, 1.065 mmol) in N,N-dimethyl formamide (5 ml), and the mixture was stirred at room temperature for 6 hours. Water was added to the mixture, and the mixture was extracted with chloroform. The organic layer was washed with brine, dried over anhydrous sodium sulfate, filtered, and concentrated under reduced pressure. The residue was purified on silica gel column chromatography (chloroform/methanol 20/1) to obtain the title compound (159 mg, 50%).
$^1$H-NMR (CDCl$_3$) δ 0.83 (t, J=7.3 Hz, 3H), 1.15-1.48 (m, 4H), 1.58-1.68 (m, 21H), 1.94-2.15 (m, 20H), 2.25-2.32 (m, 2H), 2.32 (s, 3H), 2.40-2.48 (m, 2H), 3.37-3.80 (m, 12H), 3.93 (s, 3H), 3.99-4.05 (m, 1H), 4.65 (brs, 2H), 4.80 (br, 1H), 5.07-5.18 (m, 6H), 6.86 (dd, J=7.8, 1.4 Hz, 1H), 6.97-7.00 (m, 2H). MS (ESI+): [M+H]$^+$ 893.6

Example 4

4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide

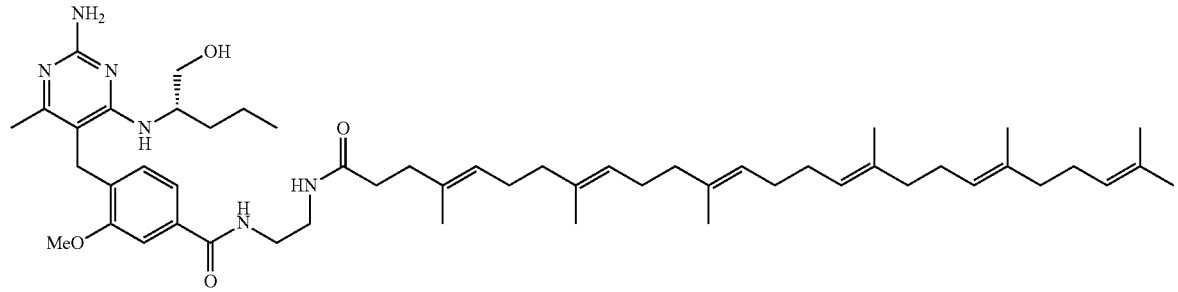 [SMILES: CCC[C@@H](CO)Nc1nc(N)nc(C)c1Cc1ccc(C(=O)NCCNC(=O)CC/C(C)=C/CC/C(C)=C/CC/C(C)=C/CC/C=C(\C)CC/C=C(\C)CCC=C(C)C)cc1OC]

Step 1

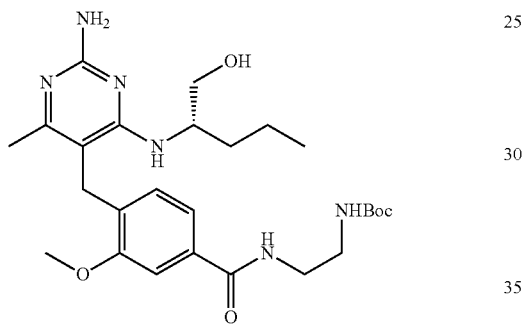

The title compound (216 mg, 78%) was obtained, in the similar manner as Step 1 of Example 3, using (S)-4-((2-amino-4-((1-hydroxypentan-2-yl)amino)-6-methylpyrimidin-5-yl)methyl)-3-methoxybenzoic acid (0.14 g, 0.41 mmol), which was prepared as described in WO2012/066336, and tert-butyl (2-aminoethyl)carbamate (137 mg, 0.855 mmol).

$^1$H-NMR (CDCl$_3$) δ 0.81 (t, J=7.3 Hz, 3H), 1.07-1.40 (m, 4H), 1.47 (s, 9H), 2.32 (s, 3H), 3.37-3.45 (m, 3H), 3.52-3.57 (m, 2H), 3.63-3.67 (m, 1H), 3.74 (s, 2H), 3.97 (s, 3H), 3.97-4.03 (m, 1H), 4.58 (br, 2H), 4.75-4.77 (br, 1H), 4.97-4.99 (br, 1H), 6.95-6.98 (m, 1H), 7.22-7.23 (m, 1H), 7.27-7.31 (br, 1H), 7.47-7.49 (m, 1H).

Step 2

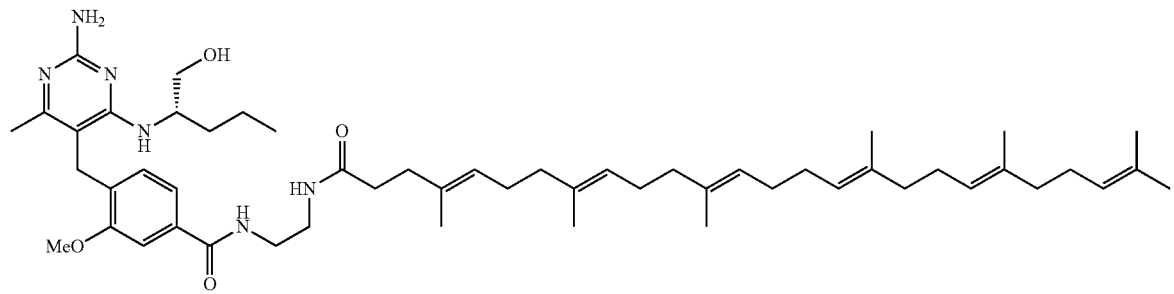 [SMILES: CCC[C@@H](CO)Nc1nc(N)nc(C)c1Cc1ccc(C(=O)NCCNC(=O)CC/C(C)=C/CC/C(C)=C/CC/C(C)=C/CC/C=C(\C)CC/C=C(\C)CCC=C(C)C)cc1OC]

The title compound (84.0 mg, 24%) was obtained, in the similar manner as Step 2 of Example 3, using the compound obtained in Step 1 (205 mg, 0.397 mmol).

$^1$H-NMR (CDCl$_3$) δ 0.81 (t, J=7.3 Hz, 3H), 1.07-1.46 (m, 4H), 1.55-1.70 (m, 21H), 1.90-2.10 (m, 20H), 2.26-2.30 (m, 4H), 2.33 (s, 3H), 3.38-3.44 (m, 1H), 3.46-3.58 (m, 4H), 3.62-3.67 (m, 1H), 3.74 (s, 2H), 3.97 (s, 3H), 3.97-4.03 (m, 1H), 4.54-4.57 (br, 2H), 4.76-4.79 (br, 1H), 5.06-5.15 (m, 6H), 6.10-6.14 (br, 1H), 7.00 (d, J=8.0 Hz, 1H), 7.24 (dd, J=8.0, 1.6 Hz, 1H), 7.38-7.41 (br, 1H), 7.45 (d, J=1.6 Hz, 1H). MS (ESI+): [M+H]$^+$ 867.6.

Example 5

4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide

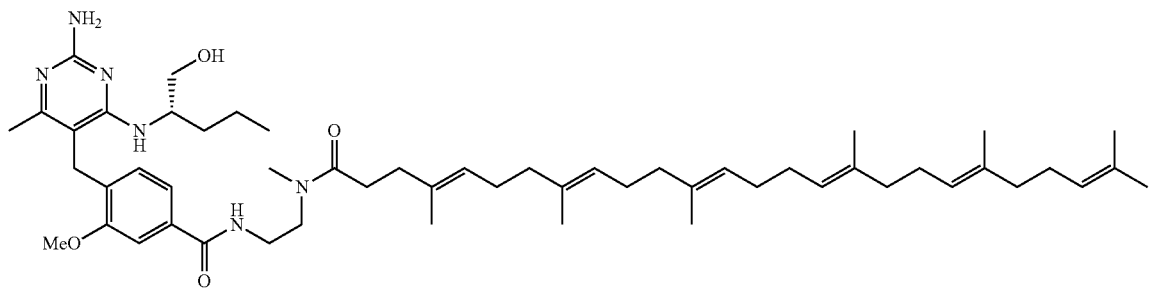 [SMILES: CCC[C@@H](CO)Nc1nc(N)nc(C)c1Cc1ccc(C(=O)NCCN(C)C(=O)CC/C(C)=C/CC/C(C)=C/CC/C(C)=C/CC/C=C(\C)CC/C=C(\C)CCC=C(C)C)cc1OC]

Step 1

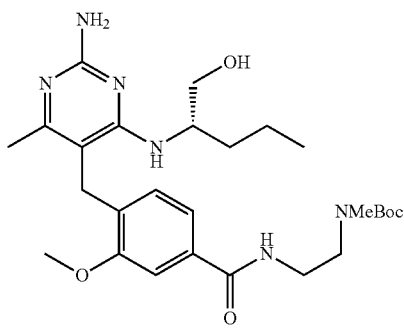

The title compound (242 mg, 81%) was obtained, in the similar manner as Step 1 of Example 3, using (S)-4-((2-amino-4-((1-hydroxypentan-2-yl)amino)-6-methylpyrimidin-5-yl)methyl)-3-methoxybenzoic acid (0.14 g, 0.41 mmol), which was prepared as described in WO2012/066336, and N-(2-aminoethyl)-N-methyl carbamic acid t-butyl ester (98 mg, 0.561 mmol).

$^1$H-NMR (CDCl$_3$) δ 0.84 (t, J=7.3 Hz, 3H), 1.07-1.41 (m, 4H), 1.43 (s, 9H), 2.31 (s, 3H), 2.91 (s, 3H), 3.39-3.44 (m, 1H), 3.45-3.55 (m, 2H), 3.56-3.61 (m, 2H), 3.62-3.67 (m, 1H), 3.73 (s, 2H), 3.96 (s, 3H), 3.97-4.02 (m, 1H), 4.55-4.59 (br, 2H), 4.74-4.78 (br, 1H), 6.94-6.97 (m, 1H), 7.21-7.24 (m, 1H), 7.47-7.50 (m, 2H).

Step 2

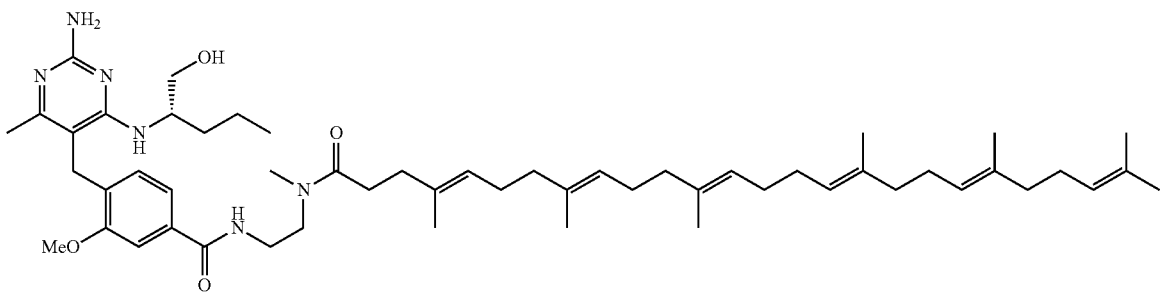 [SMILES: CCC[C@@H](CO)Nc1nc(N)nc(C)c1Cc1ccc(C(=O)NCCN(C)C(=O)CC/C(C)=C/CC/C(C)=C/CC/C(C)=C/CC/C=C(\C)CC/C=C(\C)CCC=C(C)C)cc1OC]

The title compound (149 mg, 38%) was obtained, in the similar manner as Step 2 of Example 3, using the compound obtained in Step 1 (236 mg, 0.445 mmol).

$^1$H-NMR (CDCl$_3$) δ 0.80 (t, J=7.3 Hz, 3H), 1.06-1.45 (m, 4H), 1.56-1.68 (m, 21H), 1.90-2.09 (m, 20H), 2.21-2.31 (m, 2H), 2.33 (s, 3H), 2.37-2.43 (m, 2H), 3.08 (s, 3H), 3.37-3.45 (m, 1H), 3.55-3.69 (m, 5H), 3.73 (s, 2H), 3.96 (s, 3H), 3.97-4.03 (m, 1H), 4.55-4.58 (br, 2H), 4.77-4.80 (br, 1H), 5.06-5.14 (m, 6H), 7.00 (d, J=8.0 Hz, 1H), 7.24 (dd, J=8.0, 1.2 Hz, 1H), 7.44 (d, J=1.6 Hz, 1H), 7.53-7.55 (br, 1H). MS (ESI+): [M+H]$^+$ 881.6

Test Example 1

For the first immunization, an equal volume mixture (100 μL/mouse) of ovalbumin (OVA) (1 mg/mL) and a compound of the above Examples (0.1 mg/mL) was administered intramuscularly to gastrocnemius muscle of C57BL/6 mouse. Two weeks later, an equal amount of the same mixture was administered intramuscularly to the gastrocnemius muscle for booster immunization. One week after the booster immunization, cardiac blood was collected under isoflurane inhalation anesthesia, and plasma was collected by centrifugation. OVA-specific IgG value in plasma was measured by ELISA using mouse anti-ovalbumin IgG ELISA kit (Alpha Diagnostic) (See FIG. 1).

Figure 2:
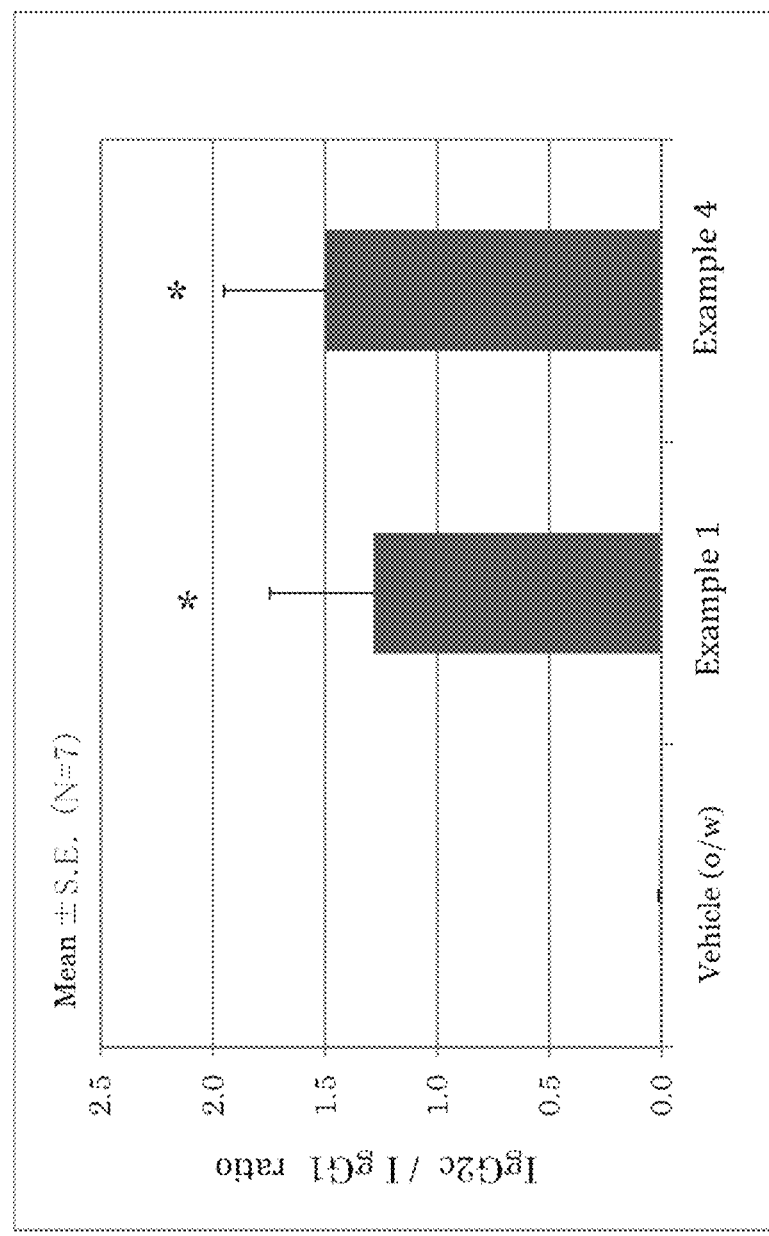
FIG. 2 shows the results of ELISA for OVA-specific IgG1 and IgG2c in plasma of immunized mice which were administered intramuscularly with the compounds of Example 1 and Example 4. The vertical axis represents OVA specific IgG2c/IgG1 ratio in plasma.

Also, the OVA-specific IgG1 and IgG2c values in the immunized mouse plasma were determined by ELISA method. Specifically, OVA solution (SIGMA) was added to a 96-well plate, followed by blocking with 1% skim milk (Wako Pure Chemical Industries, Ltd.). A plasma sample, which was diluted with phosphate buffer, and then a secondary antibody (goat anti-mouse IgG1 (Jackson) or IgG2c (Southern Bio)) were added. SureBlue™ TMB microwell peroxidase substrate (KPL) was added, and the product of the enzyme reaction was measured by microplate reader (See FIG. 2).

All of the compounds of Examples 1 to 5 induced OVA-specific IgG more strongly as compared with the negative control group. In particular, the compounds of Example 1 and Example 4 induced significant OVA-specific IgG production, as compared with the negative control group. Furthermore, the compounds of Example 1 and Example 4 significantly increased the ratio of IgG2c (one of Th1-type IgGs) to IgG1 (one of Th2-type IgGs), as compared with the negative control group.

Test Example 2

Figure 3:
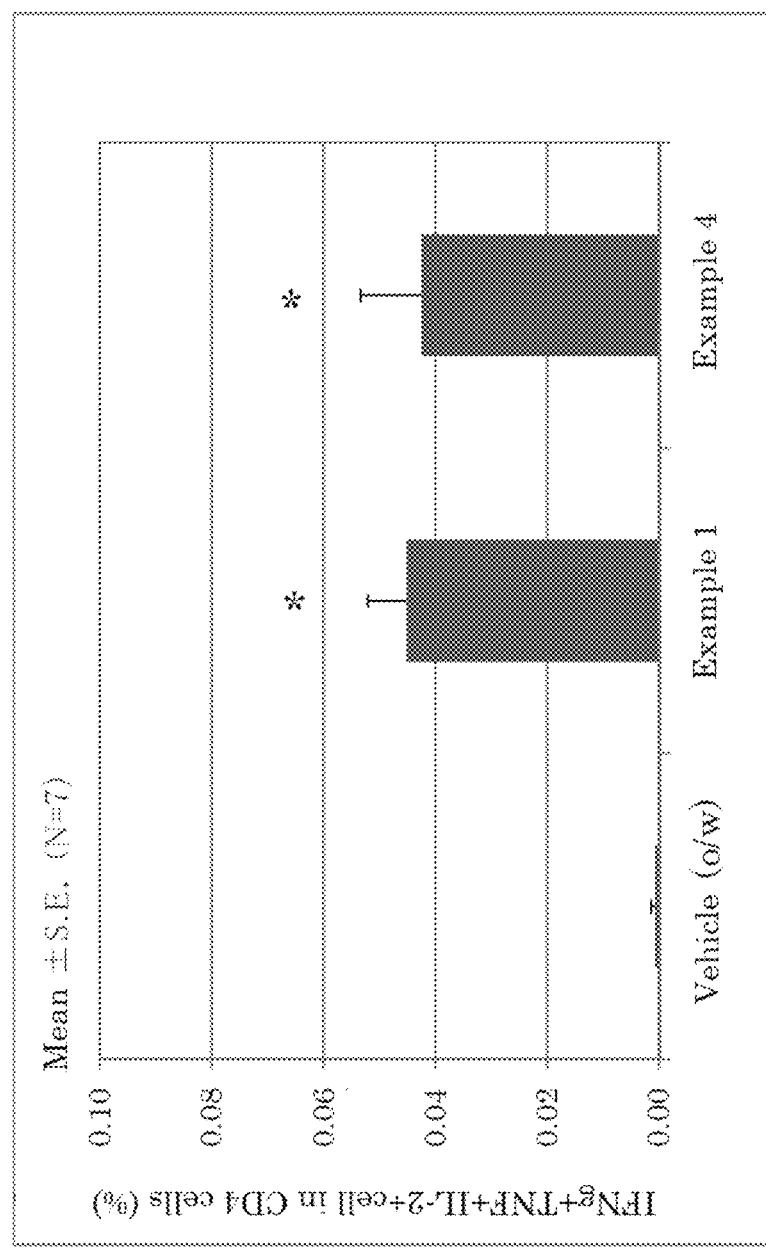
FIG. 3 shows the percentage of OVA-specific multifunctional CD4-positive T lymphocytes in spleen cells of mice which were administered intramuscularly with the compounds of Example 1 and Example 4.

The spleen cells were prepared from the mouse of Test Example 1. The cells were added with OVA and Brefeldin A (eBioscience) and cultured overnight. The cultured cells were harvested, stained with APC-labeled anti-mouse CD3e antibody, FITC-labeled anti-mouse CD4 antibody and Fixable Viability Dye Fluor® 450 (eBioscience), and fixed in Fixation/Permeabilization buffer (eBioscience). After treatment in Permeabilization buffer (eBioscience), the cells were stained with antibody cocktail PerCP-Cy5.5-labeled anti-IFN-γ antibody, PE-Cy7-labeled anti-IL-2 antibody, and PE-labeled TNF-α (eBioscience). Data acquisition and analysis were performed using FACS Cant II (BD Biosciences) and FLOWJO software (TreeStar). The results were shown in FIG. 3.

Figure 4:
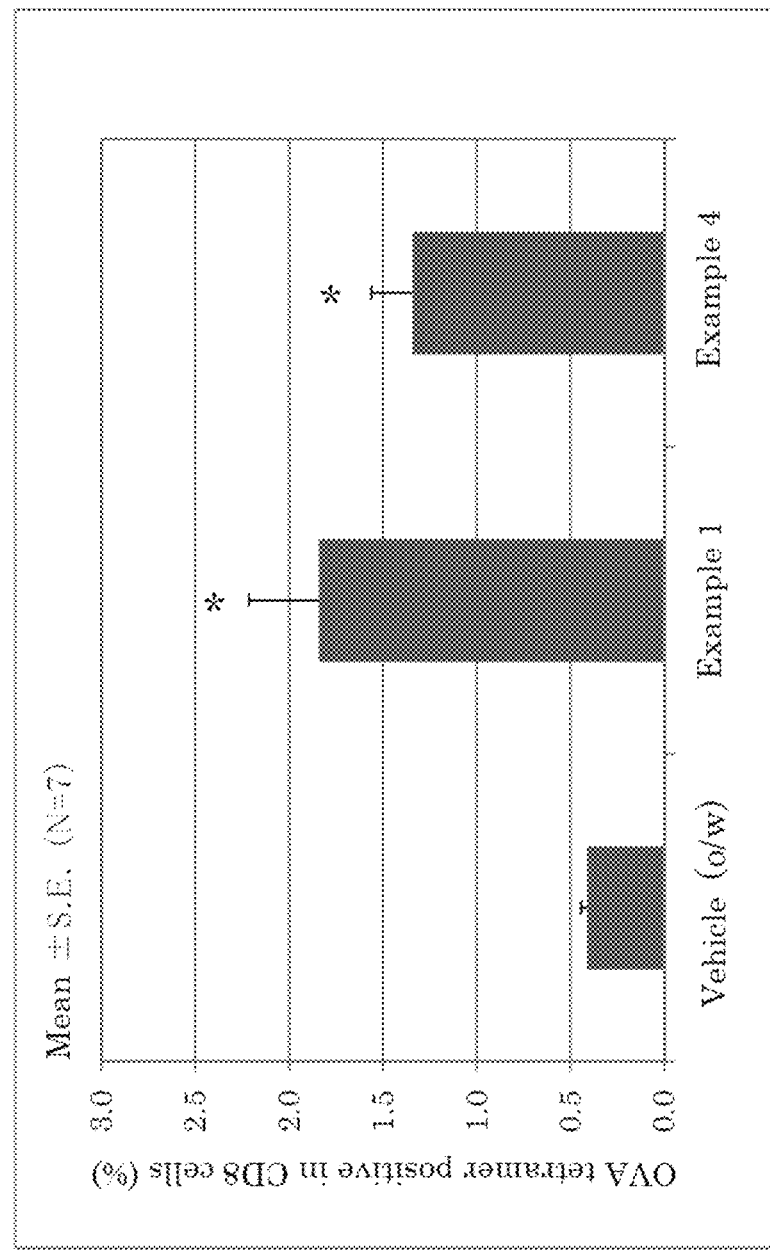
FIG. 4 shows the percentage of MHC-restricted OVA-specific CD8-positive T lymphocytes in spleen cells of mice which were administered intramuscularly with the compounds of Example 1 and Example 4.

The spleen cells were also stained with eFluor 450-labeled anti-mouse CD3e antibody, Alexa Fluor® 647-labeled anti-mouse CD8 antibody, PE-labeled H-2K$^b$ OVA Tetramer-SINFEKL (MBL) and Flexable Viability Dye eFluor 520 (eBioscience). Data acquisition and analysis were performed using FACS Cant II (BD Biosciences) and FLOWJO software (TreeStar). The results are shown in FIG. 4.

Figure 5:
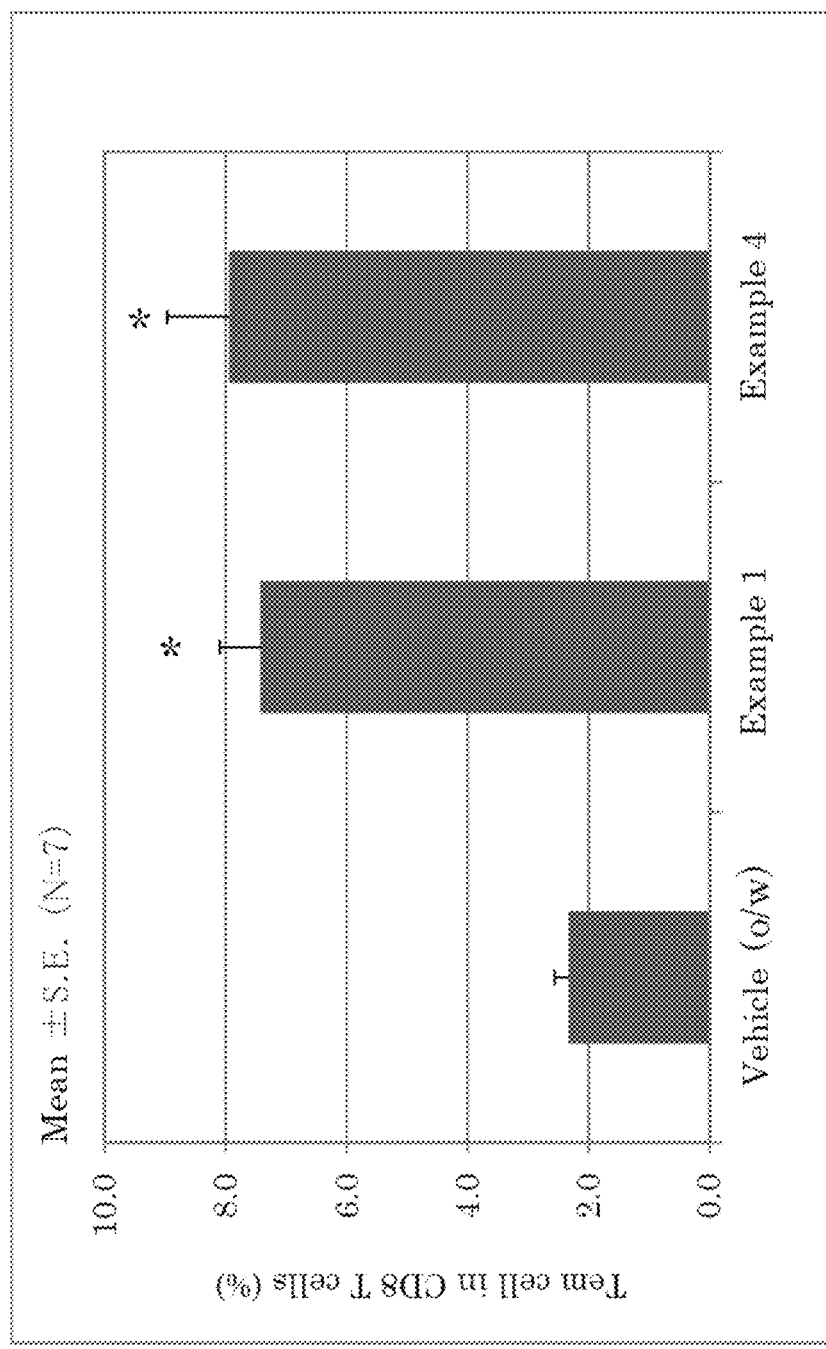
FIG. 5 shows the percentage of CD8-positive effector memory T lymphocytes in spleen cells of mice which were administered intramuscularly with the compounds of Example 1 and Example 4.

The spleen cells were further incubated with antibody cocktail eFluor450-labeled anti-mouse CD3e antibody, Alexa Fluor647-labeled anti-mouse CD8 antibody, PE-Cy7-labeled anti-mouse CD44 antibody, PerCP-Cy5.5-labeled anti-mouse CD62L antibody and Fixable Viability Dye520 (eBioscience) Data acquisition and analysis were performed using FACS Cant II (BD Biosciences) and FLOWJO software (TreeStar) The results were shown in FIG. 5.

The compounds of Example 1 and Example 4 significantly increased the proportion of OVA-specific multifunctional CD4-positive T lymphocytes, the proportion of MHC-restricted OVA-specific CD8-positive T lymphocytes, and the proportion of CD8-positive effector memory T lymphocytes, as compared with the negative control group.

INDUSTRIAL APPLICABILITY

The compound of the present invention is useful as an adjuvant, which is added to a vaccine preparation for enhancement of the immunostimulating effect.

The invention claimed is:

1. A method of inducing or enhancing an antigen-specific immune reaction in a mammal, wherein the method comprises administering to the mammal in need thereof an effective amount of a compound selected from the group consisting of:

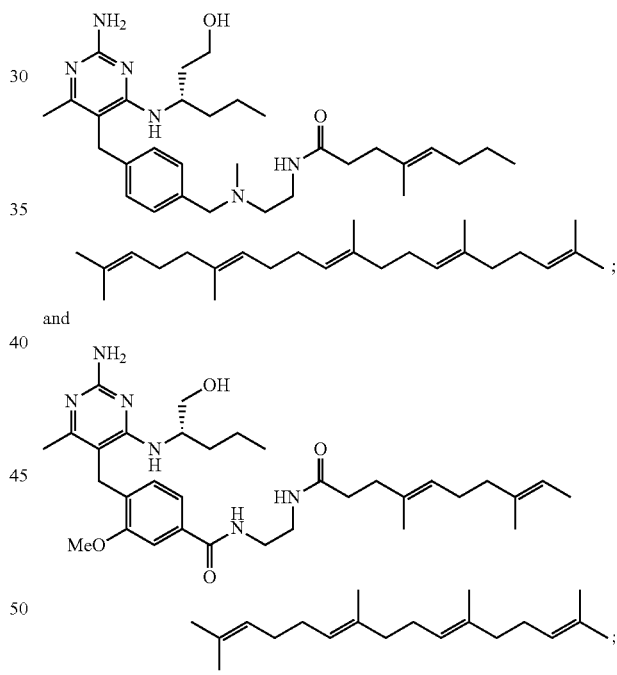

or a pharmaceutically acceptable salt thereof.

2. The method of claim 1, wherein the antigen is a pathogen-derived antigen or a tumor antigen.

3. The method of claim 1, wherein the antigen is a peptide or a protein.

4. The method of claim 1, wherein the compound activates a toll-like receptor in the mammal.

5. The method of claim 1, wherein:
   (i) the compound activates toll-like receptor (TLR7) in the mammal; or
   (ii) the compound activates toll-like receptor 8 (TLR8) in the mammal; or
   (iii) the compound activates toll-like receptor 7 (TLR7) and toll-like receptor 8 (TLR8) in the mammal.

6. The method of claim 1, wherein:
(a) the antigen-specific immune reaction in the mammal comprises an increase in CD4+ T lymphocytes in the mammal relative to a control; or
(b) the antigen-specific immune reaction in the mammal comprises an increase in CD8+ T lymphocytes in the mammal relative to a control.

7. The method of claim 6, wherein the CD8+ T lymphocytes are effector memory CD8+ T lymphocytes.

8. The method of claim 1, wherein the mammal has cancer.

9. The method of claim 1, wherein the mammal has an infectious disease.

10. A method of inducing or enhancing an antigen-specific immune reaction in a mammal, wherein the method comprises administering to the mammal in need thereof an effective amount of a compound which is:

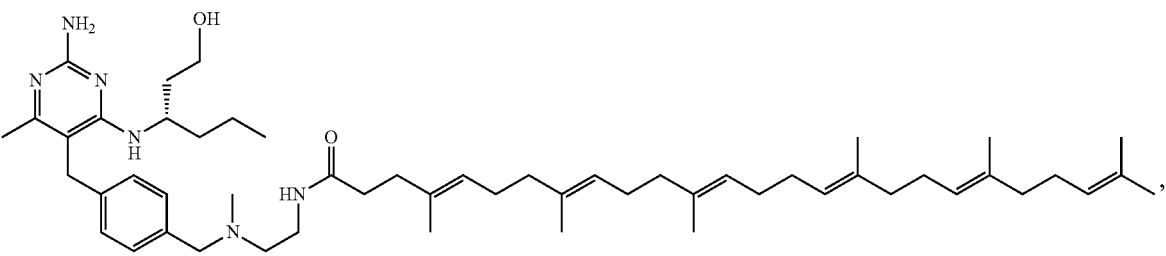 [SMILES: CCC[C@@H](CCO)Nc1nc(N)nc(C)c1Cc1ccc(CN(C)CCNC(=O)CC/C(C)=C/CC/C(C)=C/CC/C(C)=C/CC/C=C(\C)CC/C=C(\C)CCC=C(C)C)cc1]

or a pharmaceutically acceptable salt thereof.

11. The method of claim 10, wherein the antigen is a pathogen-derived antigen or a tumor antigen.

12. The method of claim 10, wherein the antigen is a peptide or a protein.

13. The method of claim 10, wherein the compound activates a toll-like receptor in the mammal.

14. The method of claim 10, wherein:
(i) the compound activates toll-like receptor 7 (TLR7) in the mammal; or
(ii) the compound activates toll-like receptor 8 (TLR8) in the mammal; or
(iii) the compound activates toll-like receptor 7 (TLR7) and toll-like receptor 8 (TLR8) in the mammal.

15. The method of claim 10, wherein:
(a) the antigen-specific immune reaction in the mammal comprises an increase in CD4+ T lymphocytes in the mammal relative to a control; or
(b) the antigen-specific immune reaction in the mammal comprises an increase in CD8+ T lymphocytes in the mammal relative to a control.

16. The method of claim 15, wherein the CD8+ T lymphocytes are effector memory CD8+ T lymphocytes.

17. The method of claim 10, wherein the mammal has cancer.

18. The method of claim 10, wherein the mammal has an infectious disease.

19. A method of inducing or enhancing an antigen-specific immune reaction in a mammal, wherein the method comprises administering to the mammal in need thereof an effective amount of a compound which is:

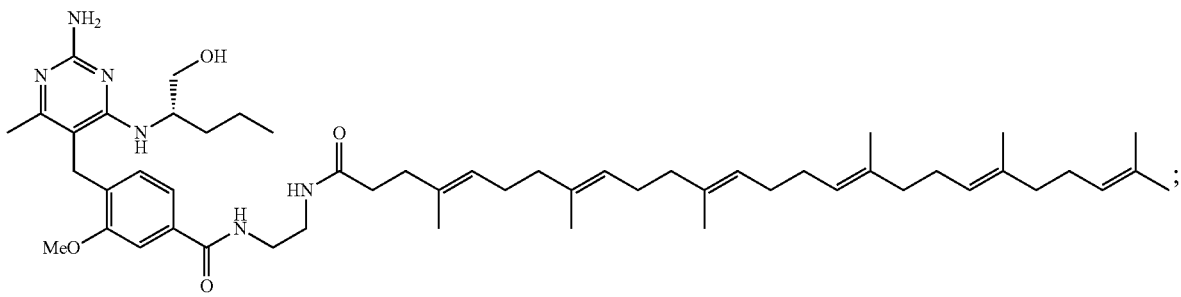

or a pharmaceutically acceptable salt thereof.

20. The method of claim 19, wherein the antigen is a pathogen-derived antigen or a tumor antigen.

21. The method of claim 19, wherein the antigen is a peptide or a protein.

22. The method of claim 19, wherein the compound activates a toll-like receptor in the mammal.

23. The method of claim 19, wherein:
   (i) the compound activates toll-like receptor 7 (TLR7) in the mammal; or
   (ii) the compound activates toll-like receptor 8 (TLR8) in the mammal; or
   (iii) the compound activates toll-like receptor 7 (TLR7) and toll-like receptor 8 (TLR8) in the mammal.

24. The method of claim 19, wherein:
   (a) the antigen-specific immune reaction in the mammal comprises an increase in CD4+ T lymphocytes in the mammal relative to a control; or
   (b) the antigen-specific immune reaction in the mammal comprises an increase in CD8+ T lymphocytes in the mammal relative to a control.

25. The method of claim 24, wherein the CD8+ T lymphocytes are effector memory CD8+ T lymphocytes.

26. The method of claim 19, wherein the mammal has cancer.

27. The method of claim 19, wherein the mammal has an infectious disease.

\* \* \* \* \*

UNITED STATES PATENT AND TRADEMARK OFFICE
CERTIFICATE OF CORRECTION

| | | |
|---|---|---|
| PATENT NO. | : 11,911,466 B2 | Page 1 of 1 |
| APPLICATION NO. | : 17/583933 | |
| DATED | : February 27, 2024 | |
| INVENTOR(S) | : Hidenori Kimura et al. | |

It is certified that error appears in the above-identified patent and that said Letters Patent is hereby corrected as shown below:

On the Title Page

Column 2 (item (56) other publications) Line 5, delete "Weinheinn:" and insert -- Weinheim: --.

In the Claims

In Column 40 Line 62, In Claim 5, after "receptor" insert -- 7 --.

Signed and Sealed this
Twenty-fourth Day of June, 2025

Coke Morgan Stewart
*Acting Director of the United States Patent and Trademark Office*